US009066981B2

(12) United States Patent
Chang et al.

(10) Patent No.: US 9,066,981 B2
(45) Date of Patent: Jun. 30, 2015

(54) ACTINICALLY-CROSSLINKABLE SILOXANE-CONTAINING COPOLYMERS

(71) Applicant: Novartis AG, Basel (CH)

(72) Inventors: Frank Chang, Cumming, GA (US); Jinyu Huang, Suwanee, GA (US); Robert Scott, Alpharetta, GA (US); Guigui Wang, Westfield, IN (US)

(73) Assignee: Novartis AG, Basel (CH)

( * ) Notice: Subject to any disclaimer, the term of this patent is extended or adjusted under 35 U.S.C. 154(b) by 54 days.

(21) Appl. No.: 14/102,741

(22) Filed: Dec. 11, 2013

(65) Prior Publication Data

US 2014/0100291 A1 Apr. 10, 2014

Related U.S. Application Data

(62) Division of application No. 12/783,592, filed on May 20, 2010, now Pat. No. 8,642,712.

(60) Provisional application No. 61/180,453, filed on May 22, 2009.

(51) Int. Cl.
*G02C 7/04* (2006.01)
*A61K 47/32* (2006.01)
*C08F 230/08* (2006.01)
*C08F 290/06* (2006.01)
*C08F 291/04* (2006.01)
*C08F 293/00* (2006.01)
*C08G 77/14* (2006.01)
*C08G 77/26* (2006.01)
*G02B 1/04* (2006.01)

(52) U.S. Cl.
CPC . *A61K 47/32* (2013.01); *G02C 7/04* (2013.01); *C08F 230/08* (2013.01); *C08F 290/068* (2013.01); *C08F 291/04* (2013.01); *C08F 293/005* (2013.01); *C08F 2438/01* (2013.01); *C08G 77/14* (2013.01); *C08G 77/26* (2013.01); *G02B 1/043* (2013.01)

(58) Field of Classification Search
CPC .................................. G02B 1/043; G02C 7/04
See application file for complete search history.

(56) References Cited

U.S. PATENT DOCUMENTS

| | | | |
|---|---|---|---|
| 4,136,250 A | 1/1979 | Mueller | |
| 4,153,641 A | 5/1979 | Deichert | |
| 4,182,822 A | 1/1980 | Chang | |
| 4,189,546 A | 2/1980 | Deichert | |
| 4,254,248 A | 3/1981 | Friends | |
| 4,259,467 A | 3/1981 | Keogh | |
| 4,260,725 A | 4/1981 | Keogh | |
| 4,261,875 A | 4/1981 | LeBoeuf | |
| 4,276,402 A | 6/1981 | Chromecek | |
| 4,327,203 A | 4/1982 | Deichert | |
| 4,341,889 A | 7/1982 | Deichert | |
| 4,343,927 A | 8/1982 | Chang | |
| 4,355,147 A | 10/1982 | Deichert | |
| 4,444,711 A | 4/1984 | Schad | |
| 4,460,534 A | 7/1984 | Boehm | |
| 4,486,577 A | 12/1984 | Mueller | |
| 4,543,398 A | 9/1985 | Bany | |
| 4,605,712 A | 8/1986 | Mueller | |
| 4,661,575 A | 4/1987 | Tom | |
| 4,684,538 A | 8/1987 | Klemarczyk | |
| 4,703,097 A | 10/1987 | Wingler | |
| 4,711,943 A | 12/1987 | Harvey, III | |
| 4,833,218 A | 5/1989 | Lee | |
| 4,837,289 A | 6/1989 | Mueller | |
| 4,954,586 A | 9/1990 | Toyoshima | |
| 4,954,587 A | 9/1990 | Mueller | |
| 5,010,141 A | 4/1991 | Mueller | |
| 5,034,461 A | 7/1991 | Lai | |
| 5,039,761 A | 8/1991 | Ono | |
| 5,070,170 A | 12/1991 | Robertson | |
| 5,079,319 A | 1/1992 | Mueller | |
| 5,227,432 A | 7/1993 | Jung | |
| 5,244,981 A | 9/1993 | Seidner | |
| 5,314,960 A | 5/1994 | Spinelli | |
| 5,314,961 A | 5/1994 | Anton | |
| 5,331,067 A | 7/1994 | Seidner | |

(Continued)

FOREIGN PATENT DOCUMENTS

CN 101215363 A 7/2008
EP 0425436 A2 5/1991

(Continued)

OTHER PUBLICATIONS

PCT International Search Report dated Jul. 14, 2010 for International Application No. PCT/US10/35495, International Filing Date May 20, 2010.
PCT Written Opinion of the International Searching Authority dated Jul. 14, 2010 for International Application No. PCT/US10/35495, International Filing Date May 20, 2010.
Extended European Search Report dated Dec. 6, 2012, for corresponding European Patent Application No. 10778355.7.

*Primary Examiner* — Margaret Moore
(74) *Attorney, Agent, or Firm* — Jian Zhou

(57) ABSTRACT

The invention provide a class of actinically-crosslinkable silicone-containing prepolymers obtained by functionalizing an intermediary copolymer to have two or more thiol or ethylenically-unsaturated groups covalently attached thereto, wherein the intermediary copolymer is an atom-transfer radical polymerization (ATRP) product of a reactive mixture comprising a polysiloxane ATRP macroinitiator and at least one hydrophilic vinylic monomer. The present invention is also related to silicone hydrogel contact lenses made from a prepolymer of the invention and methods for making the contact lenses in a cost-effective way and with high consistency and high fidelity to the original lens design.

20 Claims, No Drawings

(56) References Cited

U.S. PATENT DOCUMENTS

| | | |
|---|---|---|
| 5,346,946 A | 9/1994 | Yokoyama |
| 5,358,995 A | 10/1994 | Lai |
| 5,387,632 A | 2/1995 | Lai |
| 5,416,132 A | 5/1995 | Yokoyama |
| 5,449,729 A | 9/1995 | Lai |
| 5,451,617 A | 9/1995 | Lai |
| 5,486,579 A | 1/1996 | Lai |
| 5,508,317 A | 4/1996 | Muller |
| 5,512,205 A | 4/1996 | Lai |
| 5,527,925 A | 6/1996 | Chabrecek |
| 5,583,163 A | 12/1996 | Müller |
| 5,612,389 A | 3/1997 | Chabrecek |
| 5,612,391 A | 3/1997 | Chabrecek |
| 5,621,018 A | 4/1997 | Chabrecek |
| 5,665,840 A | 9/1997 | Pöhlmann |
| 5,712,356 A | 1/1998 | Bothe |
| 5,760,100 A | 6/1998 | Nicolson |
| 5,789,464 A | 8/1998 | Müller |
| 5,843,346 A | 12/1998 | Morrill |
| 5,849,810 A | 12/1998 | Müller |
| 5,849,811 A | 12/1998 | Nicolson |
| 5,849,841 A | 12/1998 | Mühlebach |
| 5,894,002 A | 4/1999 | Boneberger |
| 5,959,117 A | 9/1999 | Ozark |
| 5,962,548 A | 10/1999 | Vanderlaan |
| 5,981,615 A | 11/1999 | Meijs |
| 5,981,669 A | 11/1999 | Valint, Jr. |
| 5,981,675 A | 11/1999 | Valint, Jr. |
| 6,039,913 A | 3/2000 | Hirt |
| 6,165,408 A | 12/2000 | Steinmann |
| 6,221,303 B1 | 4/2001 | Steinmann |
| 6,303,687 B1 | 10/2001 | Müller |
| 6,367,929 B1 | 4/2002 | Maiden |
| 6,472,489 B1 | 10/2002 | Stockinger |
| 6,479,587 B1 | 11/2002 | Stockinger |
| 6,492,478 B1 | 12/2002 | Steinmann |
| 6,627,124 B1 | 9/2003 | Herbrechtsmeier |
| 6,719,929 B2 | 4/2004 | Winterton |
| 6,762,264 B2 | 7/2004 | Künzler |
| 6,800,225 B1 | 10/2004 | Hagmann |
| 6,822,016 B2 | 11/2004 | McCabe |
| 6,995,192 B2 | 2/2006 | Phelan |
| 7,230,051 B2 | 6/2007 | Gobelt |
| 7,238,750 B2 | 7/2007 | Müller |
| 7,256,246 B2 | 8/2007 | Kindt-Larsen |
| 7,384,590 B2 | 6/2008 | Kelly |
| 7,387,759 B2 | 6/2008 | Kelly |
| 2002/0037986 A1 | 3/2002 | Meier |
| 2004/0054071 A1 | 3/2004 | Gobelt |
| 2004/0082680 A1 | 4/2004 | Phelan |
| 2005/0113549 A1 | 5/2005 | Devlin |
| 2006/0036052 A1 | 2/2006 | Kindt-Larsen |
| 2006/0235162 A1 | 10/2006 | Muller |
| 2008/0015315 A1 | 1/2008 | Chang |
| 2008/0143958 A1 | 6/2008 | Medina |
| 2008/0174035 A1 | 7/2008 | Winterton |
| 2008/0231798 A1 | 9/2008 | Zhou |
| 2009/0230575 A1 | 9/2009 | Liu |
| 2010/0120938 A1 | 5/2010 | Phelan |

FOREIGN PATENT DOCUMENTS

| | | |
|---|---|---|
| EP | 0958315 B1 | 6/2001 |
| EP | 0932635 B1 | 7/2001 |
| EP | 0961941 B1 | 4/2002 |
| EP | 1637550 A2 | 3/2006 |
| WO | 9700274 A1 | 1/1997 |
| WO | 99/33894 | 7/1997 |
| WO | 00/31150 | 6/2000 |
| WO | 2008008752 A2 | 1/2008 |
| WO | 2008116131 A2 | 9/2008 |
| WO | 2008124093 A1 | 10/2008 |
| WO | 2009117374 A1 | 9/2009 |

ACTINICALLY-CROSSLINKABLE SILOXANE-CONTAINING COPOLYMERS

This application is a divisional application of application Ser. No. 12/783,592, filed May 20, 2010, now U.S. Pat. No. 8,642,712 which claims the benefits under 35 USC 119(e) of U.S. provisional application Ser. No. 61/180,453 filed on May 22, 2009, herein incorporated by reference in its entirety.

The present invention is related to a class of silicone-containing prepolymers and methods for making the same. In addition, the present invention is related to silicone hydrogel contact lenses made from this class of silicone-containing prepolymers.

BACKGROUND

In recent years, soft silicone hydrogel contact lenses become more and more popular because of their high oxygen permeability and comfort. Most commercially available silicone hydrogel contact lenses are produced according to a conventional cast molding technique involving use of disposable plastic molds and a mixture of monomers in the presence or absence of macromers. However, disposable plastic molds inherently have unavoidable dimensional variations, because, during injection-molding of plastic molds, fluctuations in the dimensions of molds can occur as a result of fluctuations in the production process (temperatures, pressures, material properties), and also because the resultant molds may undergo non-uniformly shrinking after the injection molding. These dimensional changes in the mold may lead to fluctuations in the parameters of contact lenses to be produced (peak refractive index, diameter, basic curve, central thickness etc.) and to a low fidelity in duplicating complex lens design.

Such disadvantages encountered in a conventional cast-molding technique can be overcome by using the so-called Lightstream Technology™ (CIBA Vision), as illustrated in U.S. Pat. Nos. 5,508,317, 5,789,464, 5,849,810, and 6,800,225, which are incorporated by reference in their entireties. The Lightstream Technology™ involves (1) a lens-forming composition which is typically a solution of one or more substantially purified prepolymer with ethylenically unsaturated groups and which generally is substantially free of monomers and crosslinking agents with a small molecular weight, (2) reusable molds produced in high precision, and (3) curing under a spatial limitation of actinic radiation (e.g., UV). Lenses produced according to the Lightstream Technology™ can have high consistency and high fidelity to the original lens design, because of use of reusable, high precision molds. In addition, contact lenses with high quality can be produced at relatively lower cost due to the short curing time and a high production yield.

These prepolymers, however, possess ill-defined structures of individual segments and usually have randomly distributed photo-crosslinkable functionalities, which causes poor reproducibility in synthesis and lens properties.

In order to fully utilize the Lightstream Technology™ to make silicone hydrogel contact lenses, there is still a need for new actinically-crosslinkable prepolymers with well-defined structures, controlled composition and molecular weight. Such prepolymers could be well suited for making silicone hydrogel contact lenses according to the Lightstream Technology™.

SUMMARY OF THE INVENTION

In one aspect, the invention provides an actinically crosslinkable prepolymer. The prepolymer of the invention is obtained by functionalizing an intermediary copolymer to have two or more actinically-crosslinkable groups covalently attached thereto, wherein the intermediary copolymer is an atom-transfer radical polymerization (ATRP) product of a reactive mixture comprising a polysiloxane ATRP macroinitiator and at least one hydrophilic vinylic monomer, wherein the actinically-crosslinkable groups are selected from the group consisting of ethylenically unsaturated groups, thiol groups, and combinations thereof.

In another aspect, the invention provides a soft contact lens made from a lens-forming material including an actinically-crosslinkable prepolymer of the invention.

In a further aspect, the invention provides a method for producing soft contact lenses from an actinically-crosslinkable prepolymer of the invention.

The invention also provides a polysiloxane ATRP macroinitiator.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"Contact Lens" refers to a structure that can be placed on or within a wearer's eye. A contact lens can correct, improve, or alter a user's eyesight, but that need not be the case. A "silicone hydrogel contact lens" refers to a contact lens comprising a silicone hydrogel material.

A "hydrogel" or "hydrogel material" refers to a polymeric material which can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

A "monomer" means a low molecular weight compound that can be polymerized. Low molecular weight typically means average molecular weights less than 700 Daltons.

An "actinically-polymerizable monomer" refers to a monomer which can be polymerized actinically. In accordance with the invention, an actinically-polymerizable monomer can be a vinylic monomer or a compound comprising two thiol groups. A compound with two thiol groups can participate in thiol-ene step-growth radical polymerization with a monomer with vinyl group to form a polymer. Step-growth radical polymerization can be used in making contact lenses, as described in a commonly-owned copending US patent application publication No. 2008/0143958 A1, herein incorporated in reference in its entirety.

"Hydrophilic," as used herein, describes a material or portion thereof that will more readily associate with water than with lipids.

A "vinylic monomer", as used herein, refers to a monomer that has one sole ethylenically unsaturated group and can be polymerized actinically or thermally.

The term "olefinically unsaturated group" or "ethylentically unsaturated group" is employed herein in a broad sense and is intended to encompass any groups containing a >C=C< group. Exemplary ethylenically unsaturated groups include without limitation acryloyl

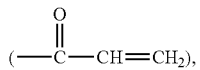

methacryloyl

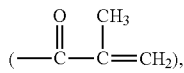

allyl, vinyl

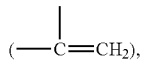

styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

The term "ATRP" refers to atom-transfer radical polymerization, as understood by a person skilled in the art.

A "polysiloxane-containing ATRP macroinitiator" refers to a polymer containing at least one polysiloxane segment and terminal organobromide or organochloride groups.

A "polysiloxane" segment refers to a divalent radical of

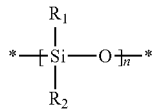

in which $R_1$ and $R_2$ are independently a monovalent $C_1$-$C_{10}$ alkyl, a monovalent $C_1$-$C_{10}$ aminoalkyl, a monovalent of $C_1$-$C_{10}$ hydroxyalkyl, $C_1$-$C_{10}$ ether, $C_1$-$C_{10}$ fluoroalkyl, $C_1$-$C_{10}$ fluoroether or $C_6$-$C_{18}$ aryl radical, -alk-(OCH$_2$CH$_2$)$_m$—OR$_3$, in which alk is $C_1$-$C_6$ alkylene divalent radical, $R_3$ is hydrogen or $C_1$-$C_6$ alkyl, and m is an integer of from 1 to 10; n is an integer of 3 or higher.

The term "fluid" as used herein indicates that a material is capable of flowing like a liquid.

A "hydrophilic vinylic monomer" refers to a vinylic monomer which can be polymerized to form a polymer that is water-soluble or can absorb at least 10 percent by weight of water.

A "hydrophobic vinylic monomer", as used herein, refers to a vinylic monomer which is polymerized to form a polymer that is insoluble in water and can absorb less than 10 percent by weight water.

A "macromer" refers to a medium and high molecular weight compound which can be polymerized and/or crosslinked. Medium and high molecular weight typically means average molecular weights greater than 700 Daltons.

An "actinically-polymerizable macromer" refers to a macromer which can be polymerized actinically. In accordance with the invention, an actinically-polymerizable macromer can be a macromer with one or more ethylenically unsaturated groups or with two or more thiol groups, which can participate in either free radical chain growth polymerization or thiol-ene step-growth radical polymerization. Preferably, a macromer contains ethylenically unsaturated groups and can be polymerized actinically or thermally.

A "vinylic macromer" refers to a macromer which can be polymerized actinically and comprises one or more ethylenically unsaturated groups.

A "prepolymer" refers to a starting polymer which contains two or more actinocally crosslinkable groups and can be cured (e.g., crosslinked) actinically to obtain a crosslinked polymer having a molecular weight much higher than the starting polymer.

A "silicone-containing prepolymer" refers to a prepolymer which contains silicone and can be crosslinked actinically to obtain a crosslinked polymer having a molecular weight much higher than the starting polymer.

"Actinically crosslinkable groups" refers to ethylenically unsaturated groups or thiol groups.

"Molecular weight" of a polymeric material (including monomeric or macromeric materials), as used herein, refers to the number-average molecular weight unless otherwise specifically noted or unless testing conditions indicate otherwise.

"Polymer" means a material formed by polymerizing one or more monomers, one or more macromers, and/or one or more prepolymers.

As used herein, the term "functionalize" in reference to a copolymer or a compound is intended to describe that one or more actinically crosslinkable groups have been covalently attached to a copolymer or compound through the pendant or terminal functional groups of the copolymer or the compound according to a coupling process.

As used herein, the term "multiple" refers to three or more.

A "photoinitiator" refers to a chemical that initiates radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types, and Irgacure® types, preferably Darocure® 1173, and Irgacure® 2959.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. A spatial limitation of UV radiation is obtained by using a mask or screen having a radiation (e.g., UV) permeable region, a radiation (e.g., UV) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation) having a cross-sectional profile defined by the projection contour of the mask or screen. The projected beam of radiation (e.g., UV radiation) limits radiation (e.g., UV radiation) impinging on a lens-forming material located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV beam (i.e., a spatial limitation of radiation). The radiation used for the crosslinking is a radiation energy, especially UV radiation, gamma radiation, electron radiation or thermal radiation, the radiation energy preferably being in the form of a substantially parallel beam in order on the one hand to achieve good restriction and on the other hand efficient use of the energy.

In the conventional cast-molding process, the first and second molding surface of a mold are pressed against each other to form a circumferential contact line which defines the edge of a result contact lens. Because the close contact of the molding surfaces can damage the optical quality of the molding surfaces, the mold cannot be reused. In contrast, in the Lightstream Technology™, the edge of a resultant contact lens is not defined by the contact of the molding surfaces of a mold, but instead by a spatial limitation of radiation. Without any contact between the molding surfaces of a mold, the mold can be used repeatedly to produce high quality contact lenses with high reproducibility.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting a lens.

"Dye" means a substance that is soluble in a lens-forming fluid material and that is used to impart color. Dyes are typically translucent and absorb but do not scatter light.

A "pigment" means a powdered substance (particles) that is suspended in a lens-forming fluid material in which it is insoluble.

"Surface modification" or "surface treatment", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, a surface treatment by energy (e.g., a plasma, a static electrical charge, irradiation, or other energy source), chemical treatments, the grafting of hydrophilic vinylic monomers or macromers onto the surface of an article, mold-transfer coating process disclosed in U.S. Pat. No. 6,719,929 (herein incorporated by reference in its entirety), the incorporation of wetting agents into a lens formulation for making contact lenses proposed in U.S. Pat. Nos. 6,367,929 and 6,822,016 (herein incorporated by references in their entireties), reinforced mold-transfer coating disclosed in U.S. Patent Application No. 60/811,949 (herein incorporated by reference in its entirety), and a hydrophilic coating composed of covalent attachment or physical deposition of one or more layers of one or more hydrophilic polymer onto the surface of a contact lens.

"Post-curing surface treatment", in reference to a silicone hydrogel material or a soft contact lens, means a surface treatment process that is performed after the formation (curing) of the hydrogel material or the soft contact lens in a mold.

A "hydrophilic surface" in reference to a silicone hydrogel material or a contact lens means that the silicone hydrogel material or the contact lens has a surface hydrophilicity characterized by having an averaged water contact angle of about 90 degrees or less, preferably about 80 degrees or less, more preferably about 70 degrees or less, more preferably about 60 degrees or less.

An "average contact angle" refers to a water contact angle (advancing angle measured by Wilhelmy Plate method), which is obtained by averaging measurements of at least 3 individual contact lenses.

An "antimicrobial agent", as used herein, refers to a chemical that is capable of decreasing or eliminating or inhibiting the growth of microorganisms such as that term is known in the art. Preferred examples of antimicrobial agent include without limitation silver salts, silver complexes, silver nanoparticles, silver-containing zeolites, and the likes "Silver nanoparticles" refer to particles which is made essentially of silver metal and have a size of less than 1 micrometer.

A "UV absorber" refers to a compound comprising a Ultraviolet absorbing ("UV-absorbing") moiety capable of absorbing or screening out UV radiation in the region of 200 to 400 nm.

The intrinsic "oxygen permeability", Dk, of a material is the rate at which oxygen will pass through a material. In accordance with the invention, the term "oxygen permeability (Dk)" in reference to a material or a contact lens means an apparent oxygen permeability which is measured with a sample (film or lens) having an average thickness over the area being measured according to a coulometric method described in Examples. Oxygen permeability is conventionally expressed in units of barrers, where "barrer" is defined as $[(cm^3 \text{ oxygen})(mm)/(cm^2)(sec)(mm\ Hg)] \times 10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as $[(cm^3 \text{ oxygen})/(cm^2)(sec)(mm\ Hg)] \times 10^{-9}$.

The "ion permeability" through a lens correlates with the Ionoflux Diffusion Coefficient. The Ionoflux Diffusion Coefficient, D (in units of $[mm^2/min]$), is determined by applying Fick's law as follows:

$$D = -n'/(A \times dc/dx)$$

where n'=rate of ion transport [mol/min]; A=area of lens exposed $[mm^2]$; dc=concentration difference [mol/L]; dx=thickness of lens [mm].

In general, the invention is directed to a class of actinically crosslinkable silicone-containing prepolymers comprising at least one polysiloxane segment and hydrophilic chain segments each terminated with an actinically crosslinkable group. Such prepolymers can be used to prepare silicone hydrogel contact lenses, in particularly according to the Lightstream Technology™ (CIBA Vision).

There are several potential unique features associated with use of prepolymers of the invention in making silicone hydrogel contact lens. First, a prepolymer of the invention has well-defined structures, controlled composition, and molecular weight. The synthesis of such prepolymer is reproducible. Lenses made from such prepolymer can have consistent properties. Second, a lens-forming formulation (polymerizable composition) can be a solution of the prepolymer which has been substantially purified (i.e., removing substantially starting materials for making the prepolymer). No lens extraction is necessary after curing of the lens. Third, a prepolymer of the invention can be cured actinically on a timescale of seconds. As such, prepolymers of the invention can fully utilize the advantages provided by the Lightstream Technology™ in make silicone hydrogel contact lenses at a relatively lower cost and at high consistency and high fidelity to the original lens design.

In one aspect, the invention provides an actinically crosslinkable prepolymer of formula (1) or (2)

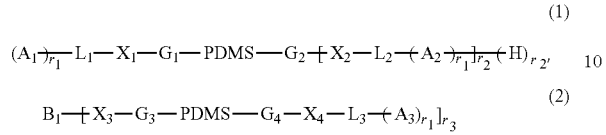

in which
- $r_1$ is an integer of 1 to 3, $r_2$ and $r_2'$ are either 0 or 1 provided that $(r_2+r_2')$ is an integer of 1,
- $r_3$ is an integer of 3 or 4;
- $G_1$, $G_2$, $G_3$, and $G_4$ independent of each other are a linear or branched $C_1$-$C_{10}$ alkylene divalent radical, a divalent radical of $-(alk'-O)_q-alk-$ in which q is an integer of from 1 to 5 and alk and alk' independent of each other is a $C_1$-$C_6$ alkylene divalent radical (or so-called divalent aliphatic hydrocarbon radical or alkyl diradical), or a divalent radical of $-R'_1-X_5-E-X_6-R'_2-$ in which $R'_1$ and $R'_2$ independent of each other is a linear or branched $C_1$-$C_{10}$ alkylene divalent radical or a divalent radical of $-(alk'-O)_q-alk-$ as defined above, $X_3$ and $X_4$ independent of each other are a linkage selected from the group consisting of

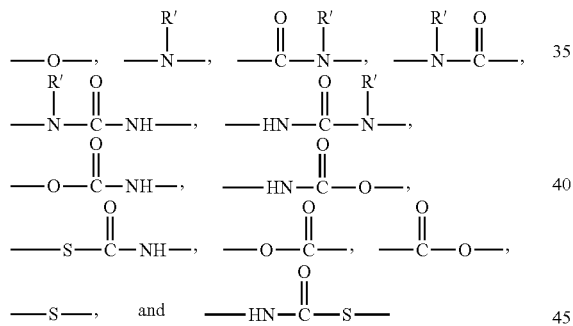

in which R' is H or $C_1$-$C_8$ alkyl, E is an alkyl diradical, a cycloalkyl diradical, an alkylcycloalkyl diradical, an alkylaryl diradical, or an aryl diradical with up to 40 carbon atoms which may have ether, thio, or amine linkages in the main chain, provided that if $r_2$ is 0, then $r_1$ is integer 2 or 3 and $G_2$ is a linear or branched $C_1$-$C_{10}$ alkyl radical or a monovalent radical of $-(alk'-O)_q-alk''$ in which q and alk' are defined as above and alk'' is $C_1$-$C_6$ alkyl;

$X_1$, $X_2$, $X_3$, and $X_4$ independent of each other are a linkage selected from the group consisting of a direct bond,

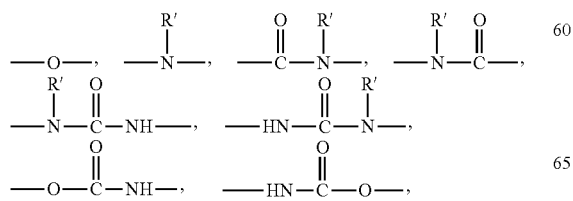

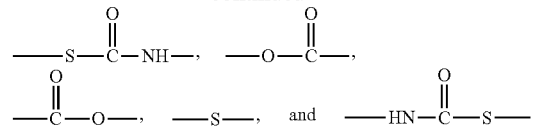

in which R' is H or $C_1$-$C_8$ alkyl;

PDMS is a polysiloxane divalent radical of formula (3)

in which v is 0 or 1, ω is an integer of from 0 to 5, $U_1$ and $U_2$ independent of each other represent a divalent radical of $-R'_1-X_5-E-X_6-R'_2-$ as defined above or a divalent radical of $-(alk'-O)_q-alk-$ as defined above, $D_1$, $D_2$ and $D_3$ independently of each other are a divalent radical selected from the group consisting of $-(CH_2CH_2O)_t-CH_2CH_2-$ in which t is an integer of 3 to 40, $-CF_2-(OCF_2)_a-(OCF_2CF_2)_b-OCF_2-$ in which a and b independent of each other is an integer of 0 to 10 provided that a+b is a number in the range of 10 to 30, and a divalent group of formula (4)

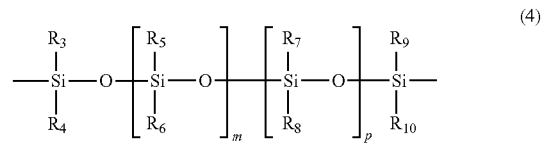

in which $R_3$, $R_4$, $R_5'$, $R_6$, $R_7$, $R_8$, $R_9$ and $R_{10}$, independently of one another, are $C_1$-$C_8$-alkyl, $C_1$-$C_4$ alkyl- or $C_1$-$C_4$-alkoxy-substituted phenyl, fluoro($C_1$-$C_{18}$-alkyl), cyano ($C_1$-$C_{12}$-alkyl), -alk-$(OCH_2CH_2)_n-OR_{11}$ in which alk is $C_1$-$C_6$-alkylene divalent radical, $R_{11}$ is $C_1$-$C_6$ alkyl and n is an integer from 1 to 10, m and p independently of each other are an integer of from 2 to 698 and (m+p) is from 5 to 700, provided that at least one of $D_1$, $D_2$ and $D_3$ is represented by formula (4);

$L_1$, $L_2$, and $L_3$ independent of each other are an organic radical having a valence of $(r_1+1)$, where the organic radical is a linear or branched $C_1$-$C_{14}$ aliphatic radical, a $C_5$-$C_{45}$ cycloaliphatic or aliphatic-cycloaliphatic di-, tri-, or tetra-valent radical, or a $C_6$-$C_{24}$ aromatic or araliphatic di-, tri-, or tetra-valent radical, provided that each of $L_1$, $L_2$, and $L_3$ has valence of $(r_1+1)$; and $B_1$ is a multivalent organic radical having a valence of $r_3$; and $A_1$, $A_2$, and $A_3$ independently of one other are a monovalent radical of formula (5)

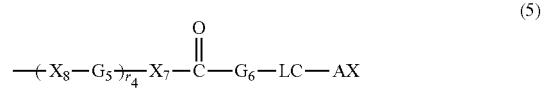

in which $r_4$ is an integer of 0 or 1; $X_7$ is

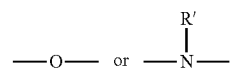

in which R' is H or $C_1$-$C_8$ alkyl; $X_8$ is a linkage selected from the group consisting of

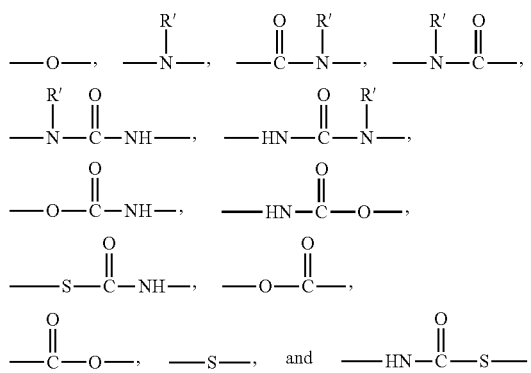

in which R' is H or $C_1$-$C_8$ alkyl; $G_5$ is a linear or branched $C_1$-$C_{10}$ alkylene divalent radical, a divalent radical of $-(-alk'-O-)_q-alk-$ as defined above, or a divalent radical of $-R'_1-X_5$-E-$X_6-R'_2-$ as defined above; $G_6$ is a $C_2$-$C_6$ alkylene divalent radical; LC is a divalent radical of a linear polymer chain of one or more hydrophilic vinylic monomers; and AX is an ethylenically unsaturated group or a thiol group.

Preferably, AX is radical of formula $-X_8$-$G_7$-$X_9$-Q, in which: $X_8$ is an linkage as defined above; $G_7$ is a direct bond or a linear or branched alkylene divalent radical; $X_9$ is a direct bond or a linkage selected from the group consisting of

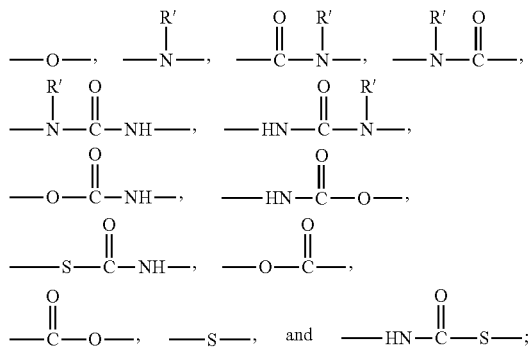

Q is an acryloyl group, a methacryloyl group, a vinyl group, an allyl group, or a norbornenyl group.

Norbornenyl group refers to a monovalent radical of hydrocarbon including a cyclohexene ring bridged with a methylene group in the para position.

A prepolymer of formula (1) or (2) can be obtained in a two-step process: (1) polymerizing, based on atom-transfer radical polymerization (ATRP), a reactive mixture comprising a polysiloxane ATRP macroinitiator and at least one hydrophilic vinylic monomer to obtain an intermediary copolymer comprising two or more hydrophilic polymer chains extending from one or both of the two ends of a polysiloxane and each hydrophilic polymer chain terminated with one bromine or chlorine atom; and (2) functionalizing the intermediary copolymer by substituting each terminal bromine or chlorine atom with a thiol or an ethylencially unsaturated group.

In accordance with a preferred embodiment of the invention, the reactive mixture comprises a polysiloxane-containing ATRP macroinitiator of formula (6) or (7)

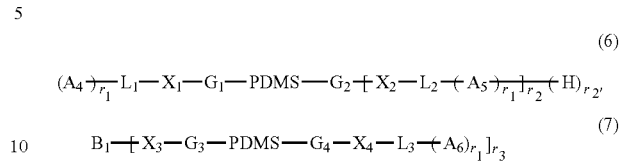

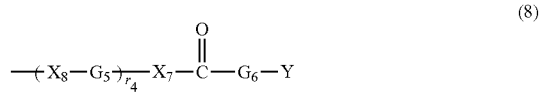

in which $G_1$, $G_2$, $G_3$, $G_4$, $X_1$, $X_2$, $X_3$, $X_4$, $L_1$, $L_2$, $L_3$, PDMS, $r_1$, $r_2$, $r_2'$, $r_3$, and $B_1$ are as defined above in formula (1) and (2); $A_4$, $A_5$, and $A_6$ independently of one another are defined formula (8)

$$-(-X_8-G_5)_{r_4}-X_7-\overset{O}{\underset{\parallel}{C}}-G_6-Y \quad (8)$$

in which Y is Br or Cl; $X_7$, $X_8$, $G_5$, $G_6$, r4 are as defined above in formula (5).

A polysiloxane ATRP macroinitiator of formula (6) can be prepared by reacting an organic dibromide or dichloride, e.g., such as, 2-chloropropionyl chloride or 2-chloroisobutyryl bromide, or preferably 2-bromopropionyl bromide or 2-bromoisobutyryl bromide, with a mono-(dihydroxyalkyl)-terminated polysiloxane, a mono-(trihydroxyalkyl)-terminated polysiloxane, a mono-(diaminoalkyl)-terminated polysiloxane, a mono-(triaminoalkyl)-terminated polysiloxane, a α,ω-bis(hydroxyalkyl)-terminated polysiloxane, a α,ω-bis(dihydroxyalkyl)-terminated polysiloxane, a α,ω-bis(trihydroxyalkyl)-terminated polysiloxane, a α,ω-bis(aminoalkyl)-terminated polysiloxane, a α,ω-bis(diaminoalkyl)-terminated polysiloxane, or a α,ω-bis(triaminoalkyl)-terminated polysiloxane.

Polysiloxanes with one hydroxyl or amino group, α,ω-bis(hydroxyalkyl)-terminated polysiloxanes, and α,ω-bis(aminoalkyl)-terminated polysiloxanes are commercially available from, e.g., from Aldrich, ABCR GmbH & Co., Fluorochem, or Gelest, Inc, Morrisville, Pa. Alternatively, they can be obtained by reacting 2-mercaptoethanol or 2-aminoethanethiol with from vinyl-terminated or acryloyl-terminated polysiloxanes of various molecular weights based on thio-ene reaction or Michael Addition reaction mechanism known to a person skilled in the art.

Polysiloxanes with one sole dihydroxyalkyl or trihydoxyalkyl terminal group can be obtained from a polysiloxane with one sole functional group well known to a person skilled in the art. For example, the amine group of 3-amino-1,2-propanediol can react with carboxylic group of a monofunctionalized polysiloxane in the presence of a carbodiimide (i.e., 1-ethyl-3-(3-dimethylaminopropyl)carbodiimide (EDC), N,N'-dicyclohexylcarbodiimide (DCC), 1-cylcohexyl-3-(2-morpholinoethyl)carbodiimide, diisopropyl carbodiimide) according to well-known carbodiimide-assisted coupling reaction, so as to form a polysiloxane with one sole dihydroxyalkyl terminal group. Alternatively, thioglycerol can react with mono-3-methacryloxypropyl terminated, mono-butyl terminated polydimethylsiloxane based on Michael Addition reaction mechanism to form a polysiloxane with one sole dihydroxyalkyl terminal group. Further, 2-mercaptoethanol can react with mono-(3-methacryloxy-2-hydroxypropyloxy)propyl terminated, mono-butyl terminated polydimethylsiloxane based on Michael Addition reaction mechanism to form a polysiloxane with one sole dihydroxyalkyl terminal group. In addition, glycerol acrylate or glycerol methacrylate can react with a monothiol-terminated, monoalkyl-terminated polysiloxane based on Michael Addition reaction mechanism to form a polysiloxane with one sole dihydroxyalkyl terminal group.

Similarly, polysiloxanes with one sole trihydroxyalkyl terminal group can be obtained by reacting N-[Tris(hydroxymethyl)methyl]acrylamide with a monothiol-terminated, monoalkyl-terminated polysiloxane, or by reacting thioglycerol with mono-(3-methacryloxy-2-hydroxypropyloxy)propyl terminated, mono-butyl terminated polydimethylsiloxane, based on Michael Addition reaction mechanism.

The above approaches can also be used to prepare α,ω-bis(dihydroxyalkyl)-terminated polysiloxanes and α,ω-bis(trihydroxyalkyl)-terminated polysiloxanes from α,ω-difunctionalized polysiloxanes.

Similarly, the above approached can be used to prepare a polysiloxane ATRP macroinitiator of formula (7). In general, the preparation of a polysiloxane ATRP macroinitiator of formula (7) involves at least two steps.

In the first step, a branching agent react with a di-functionalized polydisiloxane to form a branched polydisiloxane with three or four arms each having a terminal functional group for further reactions. A branching agent is an organic compound comprising three or four functional groups selected from the group consisting of amine groups, hydroxyl groups, carboxylic groups, isocyanate groups, thiol groups, acryloyl groups

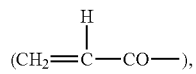

methacryloyl groups

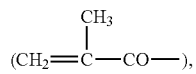

acid chloride groups, and epoxy groups. Preferably, a branching agent comprises three functional groups and a polysiloxane ATRP macroinitiator of formula (7) has three arms.

Examples of preferred branching agents include without limitation glycerol, diglycerol, 1,1,1-trishydroxymethylethane, 1,1,1-trishydroxymethylpropane, 1,2,4-butanetriol, 1,2,6-hexanetriol, erythritol, pentaerythritol, diethylenetriamine, N-2'-aminoethyl-1,3-propylenediamine, N,N-bis(3-aminopropyl)-amine, N,N-bis(6-aminohexyl)amine, triethylenetetramine, the isocyanurate trimer of hexamethylene diisocyanate, 2,4,6-toluene triisocyanate, p, p', p"-triphenylmethane triisocyanate, and the trifunctional trimer (isocyanurate) of isophorone diisocyanate, trimesoyl chloride, cyclohexane-1,3,5-tricarbonyl chloride, trimer acid chloride, triglycidylisocyanurate (TGIC), trimethylopropane trimethacrylate, pentaerythritol tetramethacrylate, triallyl isocyanurate, triallyl cyanurate, aconitic acid, citric acid, 1,3,5-cyclohexanetricarboxylic acid, 1,3,5-trimethyl-1,3,5-cyclohexanetricarboxylic acid, 1,2,3 benzene tricarboxylic acid, and 1,2,4 benzene tricarboxylic acid.

It is well known in the art that a pair of matching functional groups can form a covalent bond or linkage under known coupling reaction conditions, such as, oxidation-reduction conditions, dehydration condensation conditions, addition conditions, substitution (or displacement) conditions, Diels-Alder reaction conditions, cationic crosslinking conditions, and epoxy hardening conditions. For example, an amino group reacts with aldehyde group to form a Schiff base which may further be reduced; an amino group reacts with an acid chloride to form an amide linkage (—CO—N—); an amino group reacts with an isocyanate to form a urea linkage; an hydroxyl reacts with an isocyanate to form a urethane linkage; an hydroxyl reacts with an epoxy to form an ether linkage (—O—); a hydroxyl reacts with an acid chloride to form an ester linkage; an amino group reacts with carboxylic group in the presence of a carbodiimide to form an amide linkage, a thiol group (—SH) reacts with a vinyl group based on thiolene reaction to for a thioether linkage (—S—), a thio group reacts with an acryloyl or methacryloyl group based on Michael Addition to form a thioether linkage.

A person skilled in the art will be able to select a branching agent with three or four first functional groups and a polysiloxane with two terminal second functional groups which can react with the first functional groups to form covalent linkages based on a known coupling reaction discussed above or the like, thereby obtaining a branched polysiloxane with three or four arms.

In the second step, where the resultant branched polysiloxane with three or four polysiloxane arms has terminal hydroxyl or amine groups, it can react directly with, 2-chloropropionyl chloride, 2-chloroisobutyryl bromide, 2-bromopropionyl bromide, or 2-bromoisobutyryl bromide, to form a polysiloxane ATRP macroinitiator of formula (7). Alternatively, as discussed above, other terminal functional groups can be converted to terminal hydroxyl or amine groups or to terminal dihydroxyalkyl or trihydroxyalkyl groups or to terminal diaminoalkyl or triaminoalkyl groups. Then those resultant polysiloxanes can be reacted with 2-chloropropionyl chloride, 2-chloroisobutyryl bromide, 2-bromopropionyl bromide or 2-bromoisobutyryl bromide, to form a polysiloxane ATRP macroinitiator of formula (7).

It should be understood that the above described methods for preparing a polysiloxane ATRP macroinitiator of the invention is not exhaustive, but rather illustrative. A person skilled in the art will be able to select a known coupling method to prepare a polysiloxane ATRP macroinitiator of the invention shown in formula (6) or (7).

It is also understood that a polysiloxane can have more than one polydialkylsiloxane segment shown in formula (3), so-called a chain extended polysiloxane. Mono-functionalized and di-functionalized chain-extended polysiloxanes can be prepared according to procedures similar to those described in U.S. Pat. Nos. 4,136,250, 4,486,577, 4,605,712, 5,034,461, 5,416,132, and 5,760,100, herein incorporated by reference in their entireties.

A polysiloxane ATRP macroinitiator of the invention can be used to initiate atom-transfer radical polymerization. It is believed that in ATRP radicals are generated by the ATRP initiating moieties of a polysiloxane ATRP macroinitiator of the invention. Each ATRP initiating moiety undergoes a reversible redox process catalyzed by a transition metal compound such as cuprous halide (CuBr). Activation of the ATRP initiating moiety involves the CuBr metal center undergoing an electron transfer with simultaneous halogen atom abstraction and expansion of its coordinate sphere. The organic radical left behind after halogen atom abstraction is the reactive free radical that initiates polymerization of one or more vinylic monomers present in a reactive mixture. After the ATRP, a polymeric chain composed of the one ore more vinylic monomers is grown from each ATRP initiating moieties at the place of its halogen atom and terminated with a halogen atom. This terminal halogen atom can be used as a reactive site to covalently attach an actinically-crosslinkable group, such as an ethylencially unsaturated group (e.g., ene group or acryloyl or methacryloyl group) or a thiol group.

Nearly any hydrophilic vinylic monomer can be used in the preparation of the intermediary copolymer for making a prepolymer of the invention. Suitable hydrophilic vinylic monomers are, without this being an exhaustive list, hydrophilic amide-type vinylic monomers, hydroxyl-substituted lower alkyl($C_1$ to $C_6$) acrylates and methacrylates, hydroxyl-substituted lower alkyl vinyl ethers, N-vinylpyrrole, N-vinyl-2-pyrrolidone, 2-vinyloxazoline, 2-vinyl-4,4'-dialkyloxazolin-5-one, 2- and 4-vinylpyridine, olefinically unsaturated carboxylic acids having a total of 3 to 6 carbon atoms, amino (lower alkyl)- (where the term "amino" also includes quaternary ammonium), mono(lower alkylamino)(lower alkyl) and di(lower alkylamino)(lower alkyl)acrylates and methacrylates, allyl alcohol, N-vinyl alkylamide, N-vinyl-N-alkylamide, 1-alkyl-3-methylene-2-pyrrolidone, 1-alkyl-5-methylene-2-pyrrolidone, and 5-alkyl-3-methylene-2-pyrrolidone, and the like.

Examples of preferred hydrophilic vinylic monomers are N,N-dimethylacrylamide (DMA), N,N-dimethylmethacrylamide (DMMA), 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, dimethylaminoethyl methacrylate (DMAEMA), glycerol methacrylate (GMA), N-vinyl-2-pyrrolidone (NVP), allyl alcohol, vinylpyridine, acrylic acid, a $C_1$-$C_4$-alkoxy polyethylene glycol(meth)acrylate having a weight average molecular weight of up to 1500, methacrylic acid, N-vinyl formamide, N-vinyl acetamide, N-vinyl isopropylamide, N-vinyl-N-methyl acetamide, allyl alcohol, N-vinyl caprolactam, and mixtures thereof. More preferably, N,N-dimethylacrylamide (DMA) or N,N-dimethylmethacrylamide (DMMA) and at least one hydrophilic vinylic monomer other than DMA or DMMA are used together used in the preparation of the intermediary copolymer for making a prepolymer of the invention.

In one preferred embodiment, an actinically-crosslinakble prepolymer of the invention is represented by formula (1) in which $r_2$ is zero, In this preferred embodiment, the prepolymer consists of one arm of polysiloxane chain having no actinically-crosslinkable terminal group and two or three arms of hydrophilic polymer chains each terminated with an actinically-crosslinkable group.

In another preferred embodiment, an actinically-crosslinakble prepolymer of the invention is represented by formula (1) in which each of $r_1$ and $r_2$ is an integer of 1. In this preferred embodiment, the prepolymer has a H-shape and consists of a polysiloxane chain or a chain-extended polysiloxane chain capped at each of its two ends with two hydrophilic polymer chains.

In another preferred embodiment, an actinically-crosslinakble prepolymer of the invention is represented by formula (2) in which $r_1$ is an tiger of 1 and $r_3$ is an integer of 3. In this preferred embodiment, the prepolymer consists of three arms radiating from a branching agent, each arm consisting of a polysiloxane or chain-extended polysiloxane chain which is connected at one of its ends to the branching agent and is capped at the other end with a hydrophilic polymer chain.

In another preferred embodiment, the hydrophilic polymer chains (LC) of an actinically-crosslinkable prepolymer of the invention is composed of monomeric units of DMA and/or one or more hydrophilic vinylic monomer other than DMA.

In another preferred embodiment, the hydrophilic polymer chains (LC) of an actinically-crosslinkable prepolymer of the invention is composed of monomeric units of NVP and/or one or more hydrophilic vinylic monomer other than NVP.

In another preferred embodiment, the hydrophilic polymer chains (LC) of an actinically-crosslinkable prepolymer of the invention is composed of monomeric units of 3-acryloylamino-1-propanol, N-hydroxyethyl acrylamide, N-[tris(hydroxymethyl)methyl]-acrylamide, 2-hydroxyethylmethacrylate (HEMA), 2-hydroxyethyl acrylate (HEA), hydroxypropyl acrylate, hydroxypropyl methacrylate (HPMA), glycerol methacrylate (GMA), allyl alcohol, a $C_1$-$C_4$-alkoxy polyethylene glycol(meth)acrylate having a weight average molecular weight of up to 1500, or a combination thereof. In this preferred embodiment, the hydrophilic polymer chains have a bottle-brush structure, i.e., short hydroxyl-containing chains extending outwardly from one main hydrophilic polymer chain.

In accordance with the invention, the reactive mixture for preparing an intermediary copolymer of the invention can further comprise one or more members selected from the group consisting of a silicone-containing vinylic monomer, a hydrophobic vinylic monomer free of silicone atom, a polymerizable UV-absorbing agent (i.e., a compound comprising a UV absorbing moiety and an ethylenically unsaturated group), a polymerizable latent UV-absorbing agent (i.e., a compound comprising a latent UV absorbing moiety and an ethylenically unsaturated group). It is understood that the weight percentage of those components should be less than about 10%, preferably less than about 5%, more preferably less than about 3% relative to the total weight of polymerization components other than polysiloxane ATRP macroinitiator.

Examples of preferred silicone-containing vinylic monomers include without limitation N-[tris(trimethylsiloxy)silylpropyl]methacrylamide, N-[tris(trimethylsiloxy)-silylpropyl]acrylamide, N-[tris(dimethylpropylsiloxy)silylpropyl] acrylamide, N-[tris(dimethylpropylsiloxy)silylpropyl] methacrylamide, N-[tris(dimethylphenylsiloxy)silylpropyl] acrylamide, N-[tris(dimethylphenylsiloxy)silylpropyl] methacrylamide, N-[tris(dimethylethylsiloxy)silylpropyl] acrylamide, N-[tris(dimethylethylsiloxy)silylpropyl] methacrylamide, N-(2-hydroxy-3-(3-(bis(trimethylsilyloxy) methylsilyl)propyloxy)propyl)-2-methyl acrylamide; N-(2-hydroxy-3-(3-(bis(trimethylsilyloxy)methylsilyl)propyloxy) propyl) acrylamide; N,N-bis[2-hydroxy-3-(3-(bis (trimethylsilyloxy)methylsilyl)propyloxy)propyl]-2-methyl acrylamide; N,N-bis[2-hydroxy-3-(3-(bis(trimethylsilyloxy) methylsilyl)propyloxy)propyl]acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl) propyloxy)propyl)acrylamide; N,N-bis[2-hydroxy-3-(3-(tris (trimethylsilyloxy)silyl)propyloxy)propyl]-2-methyl acrylamide; N,N-bis[2-hydroxy-3-(3-(tris(trimethylsilyloxy)silyl) propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy)propyl]

acrylamide; N,N-bis[2-hydroxy-3-(3-(t-butyldimethylsilyl) propyloxy)propyl]-2-methyl acrylamide; N,N-bis[2-hydroxy-3-(3-(t-butyldimethylsilyl)propyloxy)propyl] acrylamide; 3-methacryloxy propylpentamethyldisiloxane, tris(trimethylsilyloxy)silylpropyl methacrylate (TRIS), (3-methacryloxy-2-hydroxypropyloxy)propylbis(trimethylsiloxy)methylsilane), (3-methacryloxy-2-hydroxypropyloxy)propyltris(trimethylsiloxy)silane, 3-methacryloxy-2-(2-hydroxyethoxy)-propyloxy)propylbis(trimethylsiloxy) methylsilane, N-2-methacryloxyethyl-O-(methyl-bis-trimethylsiloxy-3-propyl)silyl carbamate, 3-(trimethylsilyl) propylvinyl carbonate, 3-(vinyloxycarbonylthio)propyl-tris (trimethyl-siloxy)silane, 3-[tris(trimethylsiloxy)silyl] propylvinyl carbamate, 3-[tris(trimethylsiloxy)silyl]propyl allyl carbamate, 3-[tris(trimethylsiloxy)silyl]propyl vinyl carbonate, t-butyldimethyl-siloxyethyl vinyl carbonate; trimethylsilylethyl vinyl carbonate, and trimethylsilylmethyl vinyl carbonate). Most preferred siloxane-containing (meth) acrylamide monomers of formula (1) are N-[tris(trimethylsiloxy)silylpropyl]acrylamide, TRIS, N-[2-hydroxy-3-(3-(t-butyldimethylsilyl)propyloxy)propyl]acrylamide.

Examples of preferred hydrophobic vinylic monomers include methylacrylate, ethyl-acrylate, propylacrylate, isopropylacrylate, cyclohexylacrylate, 2-ethylhexylacrylate, methylmethacrylate, ethyl methacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

Any suitable polymerizable UV-absorbing agents can be used in the invention. Preferably, a polymerizable UV-absorbing agent comprises a benzotriazole-moiety or a benzophenone-moiety. Examples of preferred polymerizable UV absorbers include without limitation 2-(2-hydroxy-5-vinylphenyl)-2H-benzotriazole, 2-(2-hydroxy-5-acryloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butylphenyl)-5-chlorobenzotriazole, 2-(2'-hydroxy-5'-methacryloxyethylphenyl)benzotriazole, 2-(2'-hydroxy-5'-methacryloxypropylphenyl)benzotriazole, 2-hydroxy-4-acryloxy alkoxy benzophenone, 2-hydroxy-4-methacryloxy alkoxy benzophenone, allyl-2-hydroxybenzophenone, 2-hydroxy-4-methacryloxy benzophenone.

A polymerizable latent UV-absorbing agent can be prepared from a polymerizable UV-absorbing agent described above according to any known method known to a person skilled in the art. For example, a benzotriazole-moiety or a benzophenone-moiety can be reacted with a protected labile group to convert a UV-absorbing moiety into a latent UV-absorbing moiety.

For a benzotriazole-type of UV-absorbing agent, the hydroxyl radical of the phenol moiety in a benzotriazole moiety can be replaced with a protective labile group to render the agent essentially non-UV absorbing (i.e., the protective group essentially shifts the absorption properties of the compound so that the agent does not absorb as strongly in the 280 to 400 nm range). Examples of protective labile groups include without limitation acetyl radical, acetylalkyl-silane, alkylether, and alkylester. These protective groups can be converted back to a hydroxyl radical according to any known method after the lens is cured, thus rendering the lens UV-absorbing. For example, removal of protective labile groups can be performed by soaking the cured lens in saturated bicarbonate solution and heating.

Similarly, at least one hydroxyl radical of the phenolic radical of a benzophenone moiety can be replaced with one of the aforementioned protective labile groups to form a latent UV-absorbing moiety. The latent UV-absorbing moiety can be converted to a UV-absorbing moiety by removing the protective labile group.

A polymerizable UV-absorbing agent or a polymerizable latent UV-absorbing agent is generally is present in the monomer mixture in an amount sufficient to render a contact lens, which is obtained from the curing of the monomer mixture and is subjected to treatment to convert latent UV-absorbing moieties if applicable, absorbing at least about 80 percent of the UV light in the range of from about 280 nm to about 370 nm that impinges on the lens. A person skilled in the art will understand that the specific amount of UV-absorbing agent used in the monomer mixture will depend on the molecular weight of the UV-absorbing agent and its extinction coefficient in the range from about 280 to about 370 nm. In accordance with the invention, the monomer mixture comprises about 0.2% to about 5.0%, preferably about 0.5% to about 2.5%, by weight of a UV-absorbing agent.

A reactive mixture for preparing an intermediary copolymer of the invention preferably comprises a solvent which dissolves all of the desirable components. Example of suitable solvents includes without limitation, water, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

Where crosslinking of a prepolymer of the invention is based on the mechanism of free radical chain-growth polymerization, the actinically crosslinkable groups of the prepolymer preferably comprises at least two ethylenically unsaturated groups. For example, the bromine or chlorine atoms of an intermediary copolymer prepared according to a procedure described above can be substituted by an acryloyloxy or methacryloyloxy group if it is reacted with acrylic or methacrylic acid, by an acryloylamino or methacryloylamino group if it is reacted with acrylamide or methacrylamide, by an allylcarboxy group if it is reacted with allyl acid, or by an allylamino group if it is reacted with allylamine.

Where crosslinking of a prepolymer of the invention is based on the mechanism of thiol-ene step-growth radical polymerization, the actinically crosslinkable groups of the prepolymer preferably comprises at least two thiol groups or at least two ene-containing groups. An "ene-containing group" is intended to describe a mono-valent or divalent radical that contains a carbon-carbon double which is not directly linked to a carbonyl group (—CO—), nitrogen atom, or oxygen atom. Examples of preferred ene-groups are vinyl, allyl and norbornenyl groups. Ene-groups can be introduced into an intermediary copolymer according to any known methods. For example, the bromine or chlorine atoms of an intermediary copolymer prepared according to a procedure described above can be substituted by 5-Norbornene-2-carboxy group if it is reacted with 5-Norbornene-2-carboxylic acid.

Thiol groups can be introduced into an intermediary copolymer according to $S_N2$ displacement with a sulfur nuleophile such as thoiurea, $(NH_2)_2C=S$, as known to a person skilled in the art.

Preferably, a resultant prepolymer of the invention is substantially purified in a manner known to a person skilled in the art, for example, by precipitation with organic solvents, such as acetone, filtration and washing, extraction in a suitable solvent, dialysis or ultrafiltration, ultrafiltration being especially preferred. The prepolymers is preferably purified to be in an extremely pure form, for example in the form of concentrated solutions that are free, or at least substantially free, from reaction products, such as salts, and from starting materials, such as, for example, non-polymeric constituents. The preferred purification process for the prepolymers used in the process according to the invention, ultrafiltration, can be carried out in a manner known to a person skilled in the art. It is possible for the ultrafiltration to be carried out repeatedly, for example from two to ten times. Alternatively, the ultrafiltration can be carried out continuously until the selected degree of purity is attained. The selected degree of purity can in principle be as high as desired. By using such prepolymers in making contact lenses, the obtained lenses will not require subsequent purification such as, for example, costly and complicated extraction of unpolymerized matrix-forming material.

A prepolymer of the invention can be used in preparing silicone hydrogel contact lenses or other medical devices.

In another aspect, the invention provides a soft contact lens. The soft contact lens of the invention comprises: a silicone hydrogel material that is obtained by curing a lens-forming material in a mold, wherein the lens-forming material comprises an actinically crosslinkable prepolymer of formula (1) or (2) as described above.

In accordance with the invention, a lens-forming material is a fluid composition, which can be a solution or a melt at a temperature from about 20° C. to about 85° C. Preferably, a lens-forming material is a solution of at least one prepolymer of the invention and other desirable components in water, or an organic solvent, or a mixture of water and one or more organic solvents.

A solution of at least one prepolymer of the invention can be prepared by dissolving the prepolymer and other components in any suitable solvent known to a person skilled in the art. Examples of suitable solvents are described above.

All of the various embodiments of the prepolymer of the invention described above can be used in this aspect of the invention.

The lens-forming material can but preferably does not comprise one or more members selected from the group consisting of a hydrophilic vinylic monomer, a silicone-containing vinylic monomer, a hydrophobic vinylic monomer free of silicone atom, a crosslinking agent (i.e., compounds with two or more ethylenically unsaturated groups and with molecular weight less than 700 Daltons). However, the amount of those components should be low such that the final ophthalmic device does not contain unacceptable levels of unpolymerized vinylic monomers and/or crosslinking agents. The presence of unacceptable levels of unpolymerized monomers and/or crosslinking agents will require extraction to remove them, which requires additional steps that are costly and inefficient. But preferably, the lens-forming material is substantially free of vinylic monomer and crosslinking agent (i.e., preferably about 2% or less, more preferably about 1% or less, even more preferably about 0.5% or less by weight of combination of vinylic monomer and crosslinking agent).

All of various embodiments of hydrophilic vinylic monomers, silicone-containing vinylic monomers, and hydrophobic vinylic monomers free of silicone atoms can be used in this aspect of the invention.

Examples of preferred crosslinking agents include without limitation tetra(ethyleneglycol)diacrylate, tri(ethyleneglycol)diacrylate, ethyleneglycol diacylate, di(ethyleneglycol) diacrylate, tetraethyleneglycol dimethacrylate, triethyleneglycol dimethacrylate, ethyleneglycol dimethacylate, di(ethyleneglycol)dimethacrylate, trimethylopropane tri methacrylate, pentaerythritol tetramethacrylate, bisphenol A dimethacrylate, vinyl methacrylate, ethylenediamine dimethyacrylamide, glycerol dimethacrylate, triallyl isocyanurate, triallyl cyanurate, allylmethacrylate, dimers (e.g., 1,3-bis(methacrylamidopropyl)-1,1,3,3-tetrakis (trimethylsiloxy)disiloxane, 1,3-bis(N-methacrylamidopropyl)-1,1,3,3-tetrakis-(trimethylsiloxy) disiloxane, 1,3-bis(methacrylamidobutyl)-1,1,3,3-tetrakis (trimethylsiloxy)-disiloxane, 1,3-bis(acrylamidopropyl)-1,1, 3,3-tetrakis(trimethylsiloxy)disiloxane, 1,3-bis (methacryloxyethylureidopropyl)-1,1,3,3-tetrakis (trimethylsiloxy)disiloxane) disclosed in U.S. Pat. No. 4,711, 943 (herein incorporated by reference in its entirety), and combinations thereof. A preferred cross-linking agent is tetra (ethyleneglycol)diacrylate, tri(ethyleneglycol)diacrylate, ethyleneglycol diacylate, di(ethyleneglycol)diacrylate, triallyl isocyanurate, or triallyl cyanurate.

It must be understood that a lens-forming material can also comprise various components, such as, for example, polymerization initiators (e.g., photoinitiator or thermal initiator), a visibility tinting agent (e.g., dyes, pigments, or mixtures thereof), a polymerizable UV-absorbing agent, a polymerizable latent UV-absorbing agent, antimicrobial agents (e.g., preferably silver nanoparticles), bioactive agent, leachable lubricants, and the like, as known to a person skilled in the art.

All various embodiments of polymerizable UV-absorbing agents and polymerizable latent UV-absorbing agents can be used in this aspect of the invention.

Initiators, for example, selected from materials well known for such use in the polymerization art, may be included in the lens-forming material in order to promote, and/or increase the rate of, the polymerization reaction. An initiator is a chemical agent capable of initiating polymerization reactions. The initiator can be a photoinitiator or a thermal initiator.

A photoinitiator can initiate free radical polymerization and/or crosslinking by the use of light. Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers Examples of preferred pigments include any colorant permitted in medical devices and approved by the FDA, such as D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, etc. See Marmiom DM Handbook of U.S. Colorants for a list of colorants that may be used with the present invention. A more preferred embodiment of a pigment include (C.I. is the color index no.), without limitation, for a blue color, phthalocyanine blue (pigment blue 15:3, C.I. 74160), cobalt blue (pigment blue 36, C.I. 77343), Toner cyan BG (Clariant), Permajet blue B2G (Clariant); for a green color, phthalocyanine green (Pigment green 7, C.I. 74260) and chromium sesquioxide; for yellow, red, brown and black colors, various iron oxides; PR122, PY154, for violet, carbazole violet; for black, Monolith black C-K (CIBA Specialty Chemicals).

The bioactive agent incorporated in the polymeric matrix is any compound that can prevent a malady in the eye or reduce the symptoms of an eye malady. The bioactive agent can be a drug, an amino acid (e.g., taurine, glycine, etc.), a polypeptide, a protein, a nucleic acid, or any combination thereof. Examples of drugs useful herein include, but are not limited to, rebamipide, ketotifen, olaptidine, cromoglycolate, cyclosporine, nedocromil, levocabastine, lodoxamide, ketotifen, or the pharmaceutically acceptable salt or ester thereof. Other examples of bioactive agents include 2-pyrrolidone-5-carboxylic acid (PCA), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Examples of leachable lubricants include without limitation mucin-like materials (e.g., polyglycolic acid) and non-crosslinkable hydrophilic polymers (i.e., without ethylenically unsaturated groups).

Any hydrophilic polymers or copolymers without any ethylenically unsaturated groups can be used as leachable lubricants. Preferred examples of non-crosslinkable hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methacrylamide, a copolymer of acrylamide or methacrylamide with one or more hydrophilic vinylic monomers, polyethylene oxide (i.e., polyethylene glycol (PEG)), a polyoxyethylene derivative, poly-N—N-dimethylacrylamide, polyacrylic acid, poly 2 ethyl oxazoline, heparin polysaccharides, polysaccharides, and mixtures thereof. The number-average molecular weight $M_n$ of the non-crosslinkable hydrophilic polymer is preferably from 5,000 to 500,000, more preferably from 10,000 to 300,000, even more preferably from 20,000 to 100,000.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for preparing ocular lenses. For example, polymeric materials, such as polyethylene, polypropylene, polystyrene, PMMA, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E.

Plastics, PrimoSpire®, or the like can be used. Other materials that allow UV light transmission could be used, such as, quartz, glass, sapphire, $CaF_2$.

In a preferred embodiment, reusable molds can be used. Examples of reusable molds suitable for spatial limitation of radiation include without limitation those disclosed in U.S. Pat. Nos. 6,800,225, 6,627,124, 7,384,590, and 7,387,759, which are incorporated by reference in their entireties. In this aspect, the lens-forming material is poured into a mold consisting of two mold halves not touching each other but having a thin gap of annular design arranged between them. The gap is connected to the mold cavity, so that excess lens-forming material can flow into the gap. Instead of polypropylene molds that can be used only once, it is possible for reusable quartz, glass, sapphire or $CaF_2$ molds to be used, since, following the production of a lens, these molds can be cleaned rapidly and effectively to remove unreacted materials and other residues, using water or a suitable solvent, and can be dried with air. Reusable molds can also be made of a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual mold faces, damage as a result of contact is ruled out. This ensures a high service life of the molds, which, in particular, also ensures high reproducibility of the contact lenses to be produced and high fidelity to the lens design.

In accordance with the invention, the lens-forming material can be introduced (dispensed) into a cavity formed by a mold according to any known methods.

After the lens-forming material is dispensed into the mold, it is polymerized to produce a contact lens. Crosslinking may be initiated in the mold e.g. by means of actinic radiation, such as UV irradiation, ionizing radiation (e.g., gamma or X-ray irradiation). Where prepolymers of the invention are the polymerizable components in the lens-forming material, the mold containing the lens-forming material can be exposed to a spatial limitation of actinic radiation to crosslink the prepolymers.

The crosslinking according to the invention may be effected in a very short time, e.g. in ≤3 minutes, preferably in ≤2 minutes, more preferably in ≤1 minute, most preferably in 5 to 50 seconds.

Opening of the mold so that the molded article can be removed from the mold may take place in a manner known per se.

The molded contact lenses can further subject to further processes, such as, for example, lens extraction with an organic solvent (e.g., those described above for preparing a lens forming material), hydration (in a water or an aqueous solution of a wetting agent), surface treatment, packaging in lens packages with a packaging solution which can contain a wetting agent (e.g., a hydrophilic polymer described above) and/or a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization (e.g., autoclave); and the like.

A contact lens of the invention has an oxygen permeability of preferably at least about 40 barrers, more preferably at least about 60 barrers, even more preferably at least about 80 barrers. In accordance with the invention, an oxygen permeability is an apparent (directly measured when testing a sample with a thickness of about 100 microns) oxygen permeability according to procedures described in Examples.

A contact lens of the invention has an elastic modulus of about 2.0 MPa or less, preferably about 1.5 MPa or less, more preferably about 1.2 or less, even more preferably from about 0.4 MPa to about 1.0 MPa.

A contact lens of the invention further has an Ionoflux Diffusion Coefficient, D, of, preferably at least about $1.5 \times 10^{-6}$ $mm^2$/min, more preferably at least about $2.6 \times 10^{-6}$ $mm^2$/min, even more preferably at least about $6.4 \times 10^{-6}$ $mm^2$/min.

A contact lens of the invention further has a water content of preferably from about 15% to about 65%, more preferably from about 20% to about 50% by weight when fully hydrated. The water content of a silicone hydrogel contact lens can be measured according to Bulk Technique as disclosed in U.S. Pat. No. 5,849,811.

In a further aspect, the invention provides a method for producing soft contact lenses. The method comprises the steps of: providing a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; introduce a lens-forming material into the cavity, wherein the lens-forming material comprises an actinically crosslinkable prepolymer of formula (1) or (2) as described above; and actinically irradiating the lens forming material in the cavity to form a contact lens.

All of the various embodiments of the molds, actinically-crosslinkable prepolymers, lens-forming materials, and spatial limitation of radiation, and contact lens of the invention described above can be used in this aspect of the invention.

All of the various embodiments of the reactive mixture described above can be used in this aspect of the invention.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Oxygen Permeability Measurements

The oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H.D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm³/min., while a nitrogen stream is passed on the opposite side of the lens at a rate of about 10 to 20 cm³/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, $Dk_{app}$, is determined from the following formula:

$$Dk_{app} = Jt/(P_{oxygen})$$

where

J=oxygen flux [microliters $O_2$/cm²-minute]

$P_{oxygen}$=($P_{measured}$−$P_{water}$ vapor)=(% $O_2$ in air stream) [mm Hg]=partial pressure of oxygen in the air stream $P_{measured}$=barometric pressure (mm Hg)

$P_{water}$ vapor=0 mm Hg at 34° C. (in a dry cell) (mm Hg)

$P_{water}$ vapor=40 mm Hg at 34° C. (in a wet cell) (mm Hg)

t=average thickness of the lens over the exposed test area (mm)

where $Dk_{app}$ is expressed in units of barrers.

The oxygen transmissibility (Dk/t) of the material may be calculated by dividing the oxygen permeability ($Dk_{app}$) by the average thickness (t) of the lens.

Ion Permeability Measurements

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of 0.314×10⁻³ mm²/minute.

Water Contact Angle (WCA) Measurements

Water contact angle (WCA) measurements are performed by the *sessile* drop method with a DSA 10 drop shape analysis system from Krüss GmbH, Germany with pure water (Fluka, surface tension 72.5 mN/m at 20° C.). For measurement purposes a contact lens is taken off the storage solution with tweezers and excess storage solution is removed by gentle shaking. The contact lens are placed on the male part of a lens mold and gently blotted with a dry and clean cloth. A water droplet (approximately 1 µl) is then dosed on the lens apex, and the change of the contact angle over time of this water droplet (WCA(t), circle fitting mode) is monitored. The WCA is calculated by the extrapolation of the graph WCA(t) to t=0.

Example 2

A. Difunctional PDMS Macroinitiator

This example illustrates how to prepare prepolymers of the invention.

Scheme 1.

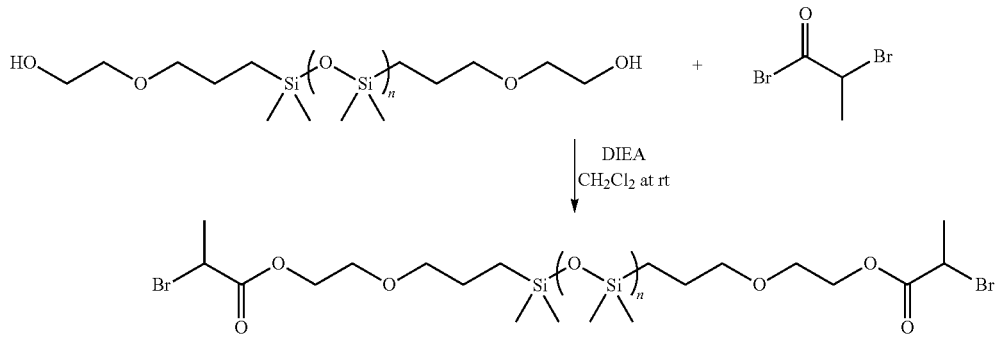

Preparation According to Scheme 1.

200 g (37 mmol) of α,ω-bis(hydroxyethoxypropyl)-terminated PDMS (KF-6003, MW≈5400 g/mol), 15.6 mL of diisopropylethylamine (90 mmol), and 1.2 L of hexanes are added in a 2 L round bottom flask. After the reaction mixture is cooled to 0° C. using an ice bath, 19.4 g (90 mmol) of 2-bromo-propionyl bromide in 60 mL of hexanes is added dropwise into the flask through an addition funnel. The reaction mixture is allowed to warm to room temperature and reacted for 12 hours with stirring. After filtration, the organic solution is washed with a saturated sodium biocarbonate solution (400 mL×2), followed by de-ionized water (400 mL×2). The organic phase is collected and dried over using anhydrous magnesium sulfate. After passing through a silica column and removing the solvent under vacuum, a slightly yellowish oil like product is collected (170 g, 85%). The product is confirmed using $^1$H NMR. The functionality is determined to be >95% (based on the $^1$H-NMR data).

B. Tertrafunctional PDMS Macroinitiator 178 g (37 mmol) of aforementioned tetra-OH terminated PDMS and 31.8 mL (222 mmol) of triethylamine are dissolved in 1 L of methylene chloride in a 2 L round bottom flask. After the reaction mixture is cooled to 0° C. using an ice bath, 23.3 ml (222 mmol) of 2-bromo-propionyl bromide in

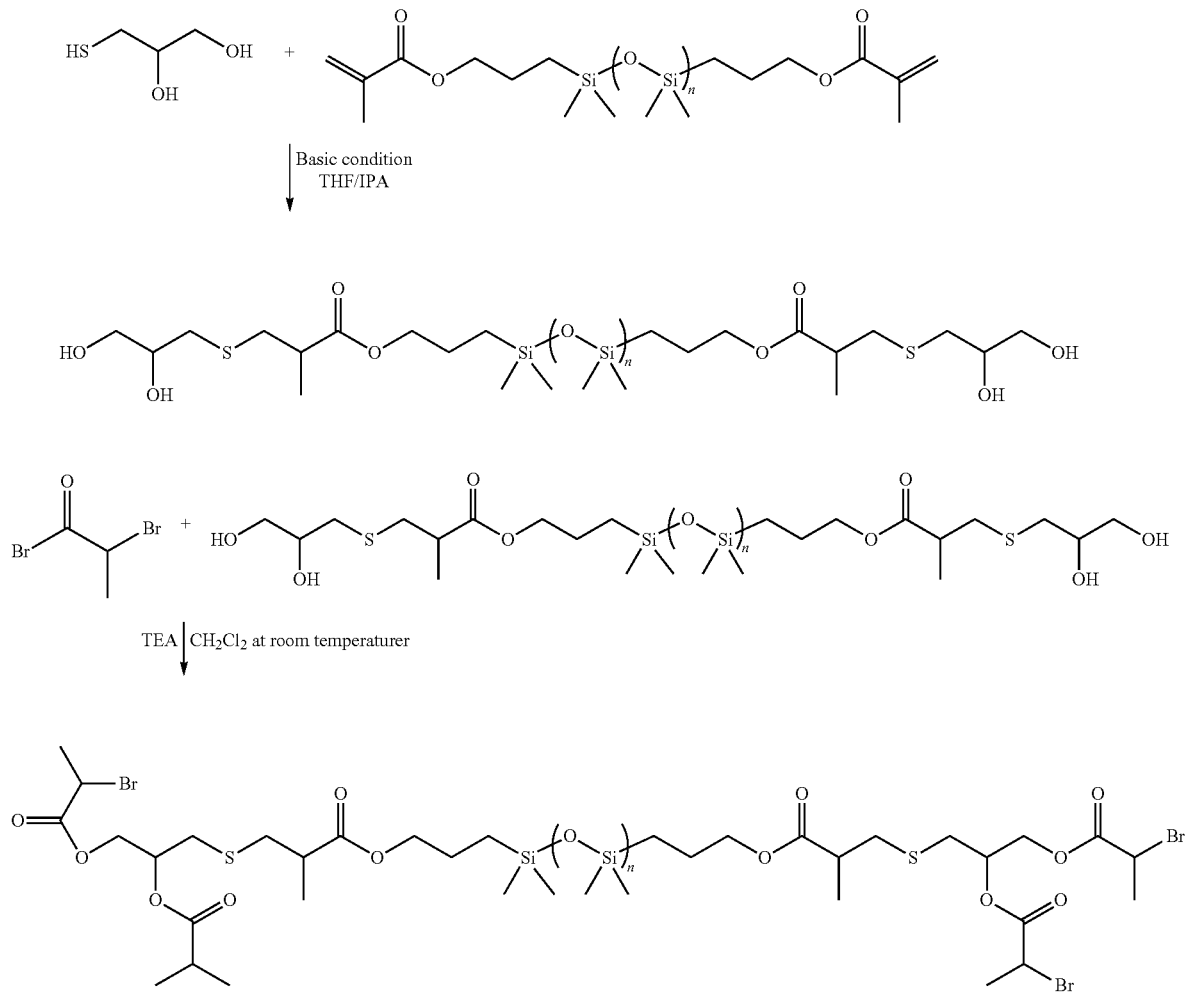

Preparation According to Scheme 2

200 g (49 mmol) of α,ω-bis(3-methacryloxypropyl)-terminated PDMS (FM7721, MW≈4100 g/mol) is dissolved in 1 L of a tetrahydrofuran/2-propanol mixture (1/1 V/V) in a 2 L round bottom flask, followed by adding 45 mL of KOH solution (0.1 N in methanol) and 17.3 g (160 mmol) of 1-thioglycerol. The reaction is carried out at room temperature and monitored by titrating with an iodine solution in water (0.1 N). After reaction for 17 h at room temperature, 45 mL of HCl solution (0.1 N in methanol) is added to neutralize the reaction solution. After removing all the solvent, the residuals are dissolved in 1 L of methylene chloride and extracted with de-ionized water (500 mL×4). The organic phase is collected and dried over anhydrous magnesium sulfate. After passing through a silica column and removing the solvent, a slightly yellowish oil like product is obtained (178 g, 89%). The functionality is determined to be greater than 95% (based on the $^1$H-NMR data).

60 mL of hexanes is added dropwise through an addition funnel. The reaction mixture is allowed to warm to room temperature and react for 16 hours. After filtration, the organic solution is washed with sodium hydroxide solution (0.037 mol/L in water, 800 ml×2) till the water layer becomes basic. The organic phase is then washed with HCl solution (pH=4, 800 mL×3) till the water layer becomes neutral, followed by deionized water (400 mL×2). The organic phase is collected and dried over anhydrous magnesium sulfate. After passing through a silica column and removing the solvent, a pale yellowish oil like product is collected (156 g, 88%). The product is confirmed by $^1$H NMR. The functionality is determined to be greater than 95% (based on the $^1$H-NMR data).

Example 3

Actinically-crosslinkable prepolymers are prepared according to scheme 3 as follows.

Scheme 3.

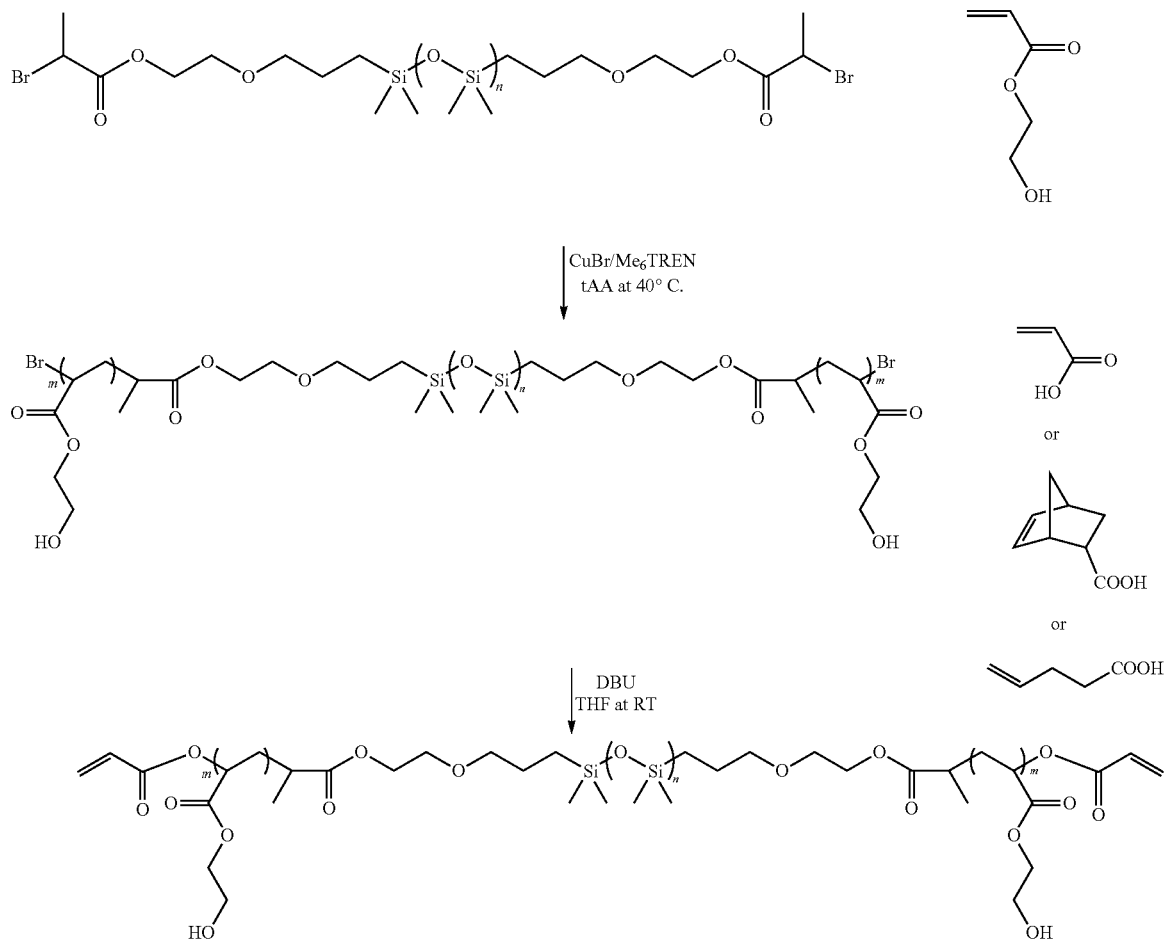

A. Synthesis of Br-PHEA-PDMS-PHEA-Br Block Copolymer 20 g (3.7 mmol) of difunctional PDMS macroinitiator (5400 g/mol) (prepared in Example 2, A), 42 mL (362 mmol) of 2-hydroxyethylacrylate (HEA), 0.04 g (0.19 mmol) of $CuBr_2$, 0.52 mL (2 mmol) of tris(2-aminoethyl amine) ($Me_6TREN$), and 160 ml of t-amyl alcohol are added to a 500 mL Schlenk flask. After four cycles of freeze-pump-thaw (20 minutes per cycle), 0.26 g (1.81 mmol) of CuBr is added to the flask under positive $N_2$ flow. The reaction is carried out at 40° C. in the oil bath. The monomer conversion is monitored by gas chromatography. At a targeted monomer conversion, the reaction is stopped by opening the flask to air. The reaction mixture is diluted with THF and passed through a neutral aluminum oxide column. After addition of 5 mg of 4-methoxyphenol, the solvent is removed by rotavap. The concentrated solution is then precipitated into acetonitrile (800 mL). After filtration, polymer (38 g) is obtained. The resultant polymer of Br-PHEA-PDMS-PHEA-Br has a molecular weight of 12,360 g/mol and 44 w % PDMS.

B. Synthesis of PHEA-PDMS-PHEA Macromer Containing Acrylate Groups 10 g (0.81 mmol) of Br-PHEA-PDMS-PHEA-Br is dissolved in 50 mL of THF in a 100 mL round bottom flask, followed by addition of 0.42 mL (6 mmol) of acrylic acid. 0.9 mL (6 mmol) of 1,8-Diazabicyclo[5,4,0]-udec-7-ene (DBU) is then slowly added to the reaction solution within 5 minutes. After reaction for 24 hours at room temperature, the polymer is purified via ultrafiltration (3K MWCO) and dried via freeze-dry. 7.5 g of final product is obtained. The MW of the prepolymer: 12360 g/mol ($^1H$ NMR); The double bond content: 0.113 meq/g (based on $^1H$ NMR).

C. Synthesis of PHEA-PDMS-PHEA Macromer Containing Norbornene Groups 10 g (0.81 mmol) of Br-PHEA-PDMS-PHEA-Br is dissolved in 50 mL of THF in a 100 mL round bottom flask, followed by addition of 0.68 mL (5.6 mmol) of 5-Norbornene-2-carboxylic acid. 0.83 mL (5.6 mmol) of 1,8-Diazabicyclo[5,4,0]-udec-7-ene (DBU) is then slowly added to the reaction solution within 5 minutes. After reaction for 24 hours, the polymer is purified via ultrafiltration (3K MWCO) and dried via freeze-dry. 7.5 g of final product is obtained. The MW of the prepolymer: 12360 g/mol ($^1H$ NMR); The double bond content: 0.081 meq/g (based on $^1H$ NMR).

The same chemistry can be used for other carboxylic acid derivatives such as 4-pentenoic acid.

Example 4

Actinically-crosslinkable prepolymers are prepared according to scheme 4 as follows.

A. Synthesis of PDMS/PHEA Multiblock Copolymers 10 g (2.1 mmol) of tetrafunctional PDMS macroinitiator (4816 g/mol), 18 mL (157 mmol) of HEA, 0.04 g (0.19 mmol) of $CuBr_2$, 0.5 mL (1.9 mmol) of $Me_6TREN$, and 120 mL of t-amyl alcohol are added to a 250 ml of Schlenk flask. After 4 cycles of freeze-pump-thaw (20 minutes per cycle), 0.24 g (1.7 mmol) of CuBr is added to the flask under the positive $N_2$ flow. The reaction is carried out at 40° C. in the oil bath. The monomer conversion is monitored by gas chromatography. At a certain monomer conversion, the reaction is stopped by opening the flask to air. The reaction mixture is diluted with THF and passed through a neutral alumina oxide column. After addition of 5 mg of 4-methoxyphenol, the solvent is removed by rotavap. The concentrated solution is then precipitated into acetonitrile (800 mL). After filtration, polymer (13 g) is obtained. The obtained polymer of PDMS/PHEA multiblock copolymer has a molecular weight of 10500 g/mol (1H NMR) and 46 w % PDMS and Mn=9421 g/mol and PDI=1.45 (GPC).

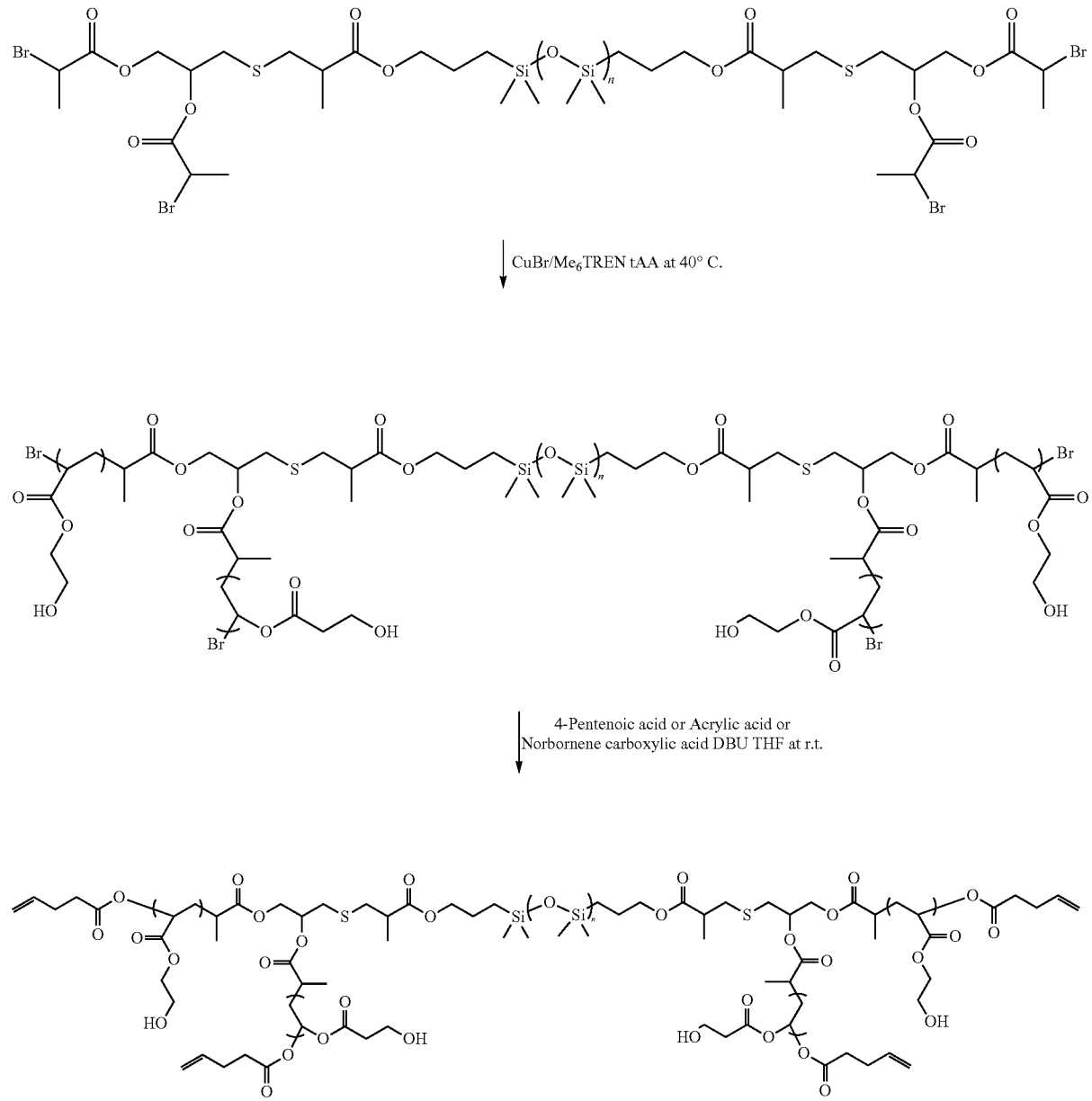

Scheme 4

B. Synthesis of PDMS/PHEA Macromer Containing Multi-Acrylate Groups 6 g (0.57 mmol) of PDMS/PHEA multiblock copolymer is dissolved in 30 mL of THF in a 100 mL round bottom flask, followed by addition of 0.37 mL (5.1 mmol) of acrylic acid. 0.76 mL (5.1 mmol) of DBU in 10 mL of THF is then slowly added to the reaction solution within 30 minutes. After reaction for 45 hours at room temperature, the solution is diluted with 600 mL of a mixture of 2-propanol and water (10 v % 2-propanol in water). The polymer is purified by ultrafiltration (3K MWCO). The final polymer powder (5 g) is obtained after freeze-dry. The MW of the prepolymer: 10386 g/mol (1H NMR); The double bond content: 0.270 meq/g (based on $^1$H NMR).

C. Synthesis of PDMS/PHEA Macromer Containing Multi-Ene Groups 14 g (1.3 mmol) of PDMS/PHEA multiblock copolymer is dissolved in 50 mL of THF in a 100 mL round bottom flask, followed by addition of 1.6 mL (15.9 mmol) of 4-pentenoic acid. 2.4 mL (15.9 mmol) of DBU in 10 mL of THF is then slowly added to the reaction solution within 30 minutes. After reaction for 45 hours at room temperature, the solution is diluted with 600 mL of a mixture of 2-propanol and water (10 v % of 2-propanol in water). The polymer is purified by dialysis (1K MWCO) in water. The final polymer powder (9.5 g) is obtained after freeze-dry. The MW of the prepolymer: 10500 g/mol (1H NMR); The double bond content: 0.358 meq/g (based on $^1$H NMR).

Example 5

A. Lenses Made from PHEA-PDMS-PHEA Macromer Containing Acrylate Groups 3 g of the prepolymer synthesized in Example 3B and 7.5 mg of Irgacure 2959 are dissolved in 15 mL of 1-propanol. After filtration through a microfilter with 5 μm pores, the solution is concentrated to 59% of solid content via rotavap. The formulation is placed in molds under UV light for 15 seconds. After removing the lens from the molds, contact lens are hydrated.

B. Lenses Made from PDMS/PHEA Prepolymer Containing Multi-Ene Groups 8.7 g (0.358 meg/g, based on 1HNMR) of the prepolymer synthesized in Example 4C and 21.8 mg of Irgacure 2959 are dissolved in 30 mL of t-amyl alcohol. After filtration through a microfilter with 5 μm pores, the solution is concentrated to 61% of solid content via rotavap. In order to obtain the stoichiometric ratio between thiol to ene, photo-rheology is carried out on small size formulation samples by varying the ratio of thiol to ene. Three 0.2 g of formulation samples are mixed with 3.65 mg, 4.01 mg, and 4.4 mg of 3,6-Dioxane-1,8-octane-dithiol, respectively. The remaining 11.43 g formulation is used for lens cast in the presence of 0.17 g (1.87 mmol) of dithiol. The formulation is placed in molds under UV light for 11 seconds. After removing the lens from the molds, contact lens are hydrated.

| Components | Formulation A | Formulation B |
|---|---|---|
| Prepolymer (Ex. 3B) | Example 3B | Example 4C |
| MW (g/mol) | 12,360 | 10,152 |
| (double bond content meq/g) | (0.113) | (0.358) |
| Macromer content (%) | 59 | 61.00 |
| Irgacure 2959 (% vs. macromer) | 0.25 | 0.25 |
| DOD | | 1.66 |
| Solvent (%) | 41 | 37 |

DOD = 3,6-Dioxane-1,8-octane-dithiol

C. Lens Characterization Results

| | Lens A | Lens B |
|---|---|---|
| Photo-curing (s) | 15 | 11 |
| Water content (%) | 57 | 42 |
| Thickness (μm) | 97 | 110 |
| Modulus (Mpa) | 0.82 | 1.85 |
| Max elongation (%) | 33 | 91 |
| Toughness (kJ/m$^3$) | 37 | 420 |

What is claimed is:

1. A soft contact lens, comprising a silicone hydrogel material which is a polymerization product of a lens-forming material, wherein the lens-forming material comprises an actinically crosslinkable prepolymer of formula (1) or (2)

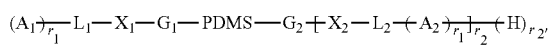

in which
  $r_1$ is an integer of 2 or 3, $r_2$ and $r_2'$ are either 0 or 1 provided that $(r_2 + r_2') = 1$, $r_3$ is an integer of 3 or 4;
  $G_1$ and $G_2$ independent of each other are a linear or branched $C_1$-$C_{10}$ alkylene divalent radical, a divalent radical of —(alk'-O—)$_q$alk- in which q is an integer of from 1 to 5 and alk and alk' independent of each other is a $C_1$-$C_6$ alkylene divalent radical, or a divalent radical of —R'$_1$—X$_5$-E-X$_6$—R'$_2$— in which R'$_1$ and R'$_2$ independent of each other is a linear or branched $C_1$-$C_{10}$ alkylene divalent radical or a divalent radical of —(alk'-O—)$_q$alk- as defined above, X$_5$ and X$_6$ independent of each other are a linkage selected from the group consisting of

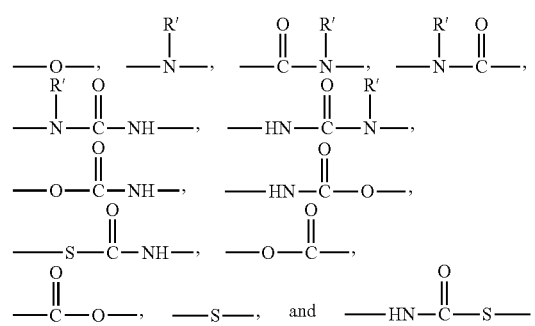

in which
  R' is H or $C_1$-$C_8$ alkyl, E is an alkyl diradical, a cycloalkyl diradical, an alkylcycloalkyl diradical, an alkylaryl diradical, or an aryl diradical with up to 40 carbon atoms which may have ether, thio, or amine linkages in the main chain, provided that if $r_2$ is 0, then $r_1$ is integer 2 or 3 and $G_2$ is a linear or branched $C_1$-$C_{10}$ alkyl radical or a monovalent radical of $-(alk'-O)_q$-alk" in which q and alk' are defined as above and alk" is $C_1$-$C_6$ alkyl;

$X_1$ and $X_2$ independent of each other are a linkage selected from the group consisting of a direct bond,

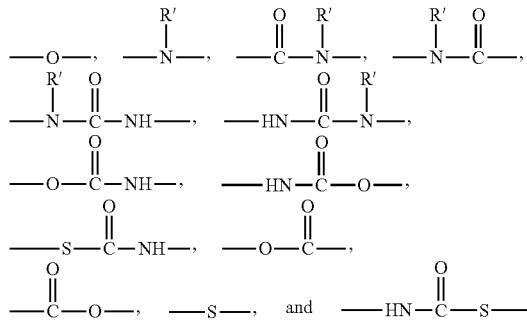

in which
R' is H or $C_1$-$C_8$ alkyl;
PDMS is a polysiloxane divalent radical of formula (3)

in which v is 0 or 1, ω is an integer of from 0 to 5, $U_1$ and $U_2$ independent of each other represent a divalent radical of $—R'_1—X_5$-$E$-$X_6—R'_2—$ as defined above or a divalent radical of $-(alk'-O)_q$-alk- as defined above, $D_1$, $D_2$ and $D_3$ independently of each other are a divalent radical selected from the group consisting of $—(CH_2CH_2O)_t$—$CH_2CH_2—$ in which t is an integer of 3 to 40, $—CF_2)_a—(OCF_2)_a—(OCF_2CF_2)_b—OCF_2—$ in which a and b independent of each other is an integer of 0 to 10 provided that a+b is a number in the range of 10 to 30, and a divalent group of formula (4)

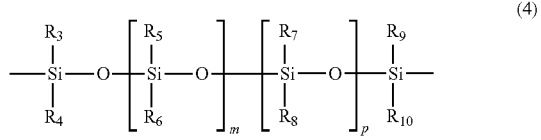

in which $R_3$, $R_4$, $R_5'$, $R_6$, $R_7$, $R_8$, $R_9$ and $R_{10}$, independently of one another, are $C_1$-$C_8$-alkyl, $C_1$-$C_4$ alkyl- or $C_1$-$C_4$-alkoxy-substituted phenyl, fluoro($C_1$-$C_{18}$-alkyl), cyano($C_1$-$C_{12}$-alkyl), -alk-$(OCH_2CH_2)_n$—$OR_{11}$ in which alk is $C_1$-$C_6$-alkylene divalent radical, $R_{11}$ is $C_1$-$C_6$ alkyl and n is an integer from 1 to 10, m and p independently of each other are an integer of from 2 to 698 and (m+p) is from 5 to 700, provided that at least one of $D_1$, $D_2$ and $D_3$ is represented by formula (4);

$L_1$ and $L_2$ independent of each other are an organic radical having a valence of ($r_1$+1), where the organic radical is a linear or branched $C_1$-$C_{14}$ aliphatic radical, a $C_5$-$C_{45}$ cycloaliphatic or aliphatic-cycloaliphatic di-, tri-, or tetra-valent radical, or a $C_6$-$C_{24}$ aromatic or araliphatic di-, tri-, or tetra-valent radical, provided that each of $L_1$ and $L_2$ has valence of ($r_1$+1); and $B_1$ is a multivalent organic radical having a valence of $r_3$; and $A_1$ and $A_2$ independently of one other are a monovalent radical of formula (5)

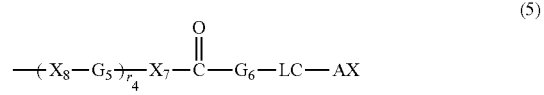

in which $r_4$ is an integer of 0 or 1; $X_7$ is

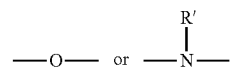

in which R' is H or $C_1$-$C_8$ alkyl; $X_8$ is a linkage selected from the group consisting of

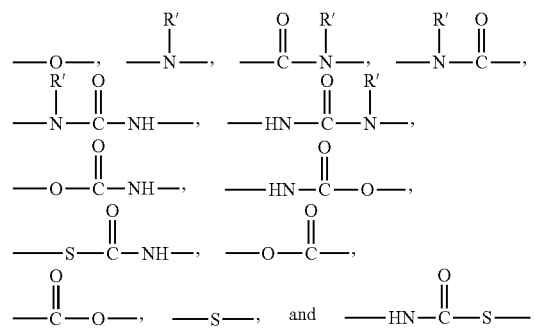

in which R' is H or $C_1$-$C_8$ alkyl; $G_5$ is a linear or branched $C_1$-$C_{10}$ alkylene divalent radical, a divalent radical of $-(alk'-O)_q$-alk- as defined above, or a divalent radical of $—R'_1—X_5$-$E$-$X_6—R'_2—$ as defined above; $G_6$ is a $C_2$-$C_6$ alkylene divalent radical; LC is a divalent radical of a linear polymer chain of one or more hydrophilic vinylic monomers; and AX is a thiol group or a radical of formula $—X_8$-$G_7$-$X_9$-Q, in which: $X_8$ is an linkage as defined above; $G_7$ is a direct bond or a linear or branched alkylene divalent radical; $X_9$ is a direct bond or a linkage selected from the group consisting of

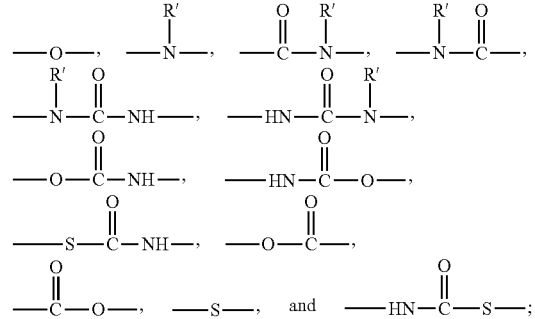

Q is an acryloyl group, a methacryloyl group, a vinyl group, an allyl group, or a norbornenyl group.

2. The contact lens of claim 1, wherein the contact lens has at least one property selected from the group consisting of an oxygen permeability of at least about 40 barrers, an elastic modulus of about 2.0 MPa or less, an Ionoflux Diffusion Coefficient, D, of at least about $1.5 \times 10^{-6}$ mm$^2$/min, and a water content of from about 15% to about 65%.

3. The contact lens of claim 1, wherein the lens-forming material comprises one or more components selected from the group consisting of a photoinitiator or thermal initiator, a visibility tinting agent, a polymerizable UV-absorbing agent, a polymerizable latent UV-absorbing agent, an antimicrobial agent, a bioactive agent, and a leachable lubricant.

4. The contact lens of claim 1, wherein the lens-forming material comprises one or more components selected from the group consisting of a hydrophilic vinyl monomer, a silicone-containing vinyl monomer, a hydrophobic vinyl monomer free of silicone atom, a crosslinking agent.

5. A method for producing soft contact lenses, comprising the steps of:
providing a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces;
introduce a lens-forming material into the cavity, wherein the lens-forming material comprises an actinically crosslinkable prepolymer of formula (1) or (2)

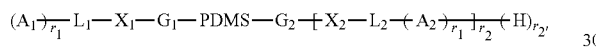 (1)

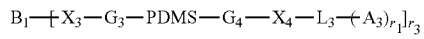 (2)

in which $r_1$ is an integer of 2 or 3 in formula (1) and in which $r_1$ is an integer of 1 to 3 in formula (2), $r_2$ and $r_2'$ are either 0 or 1 provided that $(r_2+r_2')=1$, $r_3$ is an integer of 3 or 4; $G_1$, $G_2$, $G_3$, and $G_4$ independent of each other are a linear or branched $C_1$-$C_{10}$ alkylene divalent radical, a divalent radical of a $-(\text{alk'-O})_q\text{alk-}$ in which q is an integer of from 1 to 5 and alk and alk' independent of each other is a $C_1$-$C_6$ alkylene divalent radical, or a divalent radical of $-R'_1-X_5-E-X_6-R'_2-$ in which $R'_1$ and $R'_2$ independent of each other is a linear or branched $C_1$-$C_{10}$ alkylene divalent radical or a divalent radical of $-(\text{alk'-O})_q\text{alk-}$ as defined above, $X_3$ and $X_4$ independent of each other are a linkage selected from the group consisting of

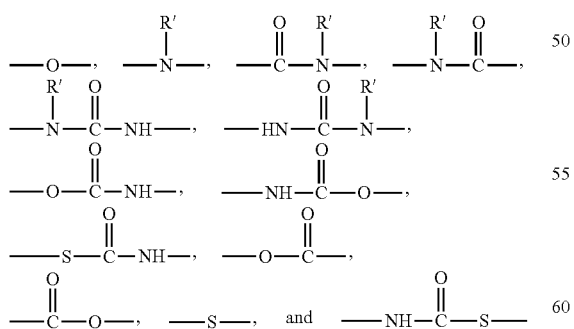

in which R' is H or $C_1$-$C_8$ alkyl, E is an alkyl diradical, a cycloalkyl diradical, an alkylcycloalkyl diradical, an alkylaryl diradical, or an aryl diradical with up to 40 carbon atoms which may have ether, thio, or amine linkages in the main chain, provided that if $r_2$ is 0, then $r_1$ is integer 2 or 3 and $G_2$ is a linear or branched $C_1$-$C_{10}$ alkyl radical or a monovalent radical of $-(\text{alk'-O})_q\text{alk''}$ in which q and alk' are defined as above and alk'' is $C_1$-$C_6$ alkyl;

$X_1$, $X_2$, $X_5$ and $X_6$ independent of each other are a linkage selected from the group consisting of a direct bond,

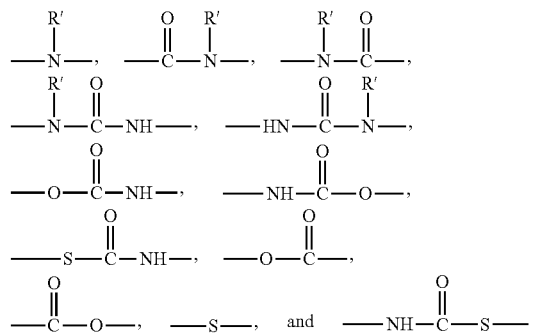

in which R' is H or $C_1$-$C_8$ alkyl;

PDMS is a polysiloxane divalent radical of formula (3)

 (3)

in which v is 0 or 1, ω is an integer of from 0 to 5, $U_1$ and $U_2$ independent of each other represent a divalent radical of $-R'_1-X_5-E-X_6-R'_2-$ as defined above or a divalent radical of $-(\text{alk'-O})_q\text{alk-}$ as defined above, $D_1$, $D_2$ and $D_3$ independently of each other are a divalent radical selected from the group consisting of $-(CH_2CH_2O)_t-CH_2CH_2-$ in which t is an integer of 3 to 40, $-CF_2-(OCF_2)_a-(OCF_2CF_2)_b-OCF_2-$ in which a and b independent of each other is an integer of 0 to 10 provided that a+b is a number in the range of 10 to 30, and a divalent group of formula (4)

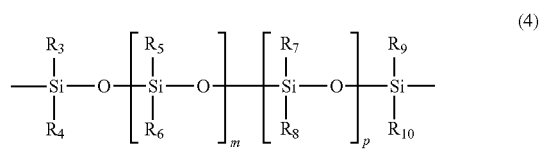 (4)

in which $R_3$, $R_4$, $R_5'$, $R_6$, $R_7$, $R_8$, $R_9$ and $R_{10}$, independently of one another, are $C_1$-$C_8$-alkyl, $C_1$-$C_4$ alkyl- or $C_1$-$C_4$-alkoxy-substituted phenyl, fluoro($C_1$-$C_{18}$-alkyl), cyano ($C_1$-$C_{12}$-alkyl), -alk-(OCH$_2$CH$_2$)$_n$—OR$_{11}$ in which alk is $C_1$-$C_6$-alkylene divalent radical, $R_{11}$ is $C_1$-$C_6$ alkyl and n is an integer from 1 to 10, m and p independently of each other are an integer of from 2 to 698 and (m+p) is from 5 to 700, provided that at least one of $D_1$, $D_2$ and $D_3$ is represented by formula (4);

$L_1$, $L_2$, and $L_3$ independent of each other are an organic radical having a valence of $(r_1+1)$, where the organic radical is a linear or branched $C_1$-$C_{14}$ aliphatic radical, a $C_5$-$C_{45}$ cycloaliphatic or aliphatic-cycloaliphatic di-, tri-, or tetra-valent radical, or a $C_6$-$C_{24}$ aromatic or araliphatic di-, tri-, or tetra-valent radical, provided that each of $L_1$, $L_2$, and $L_3$ has valence of $(r_1+1)$; and $B_1$ is a multivalent organic radical having a valence of $r_3$; and $A_1$, $A_2$, and $A_3$ independently of one other are a monovalent radical of formula (5)

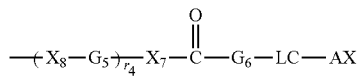

in which $r_4$ is an integer of 0 or 1; $X_7$ is

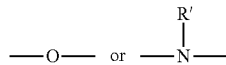

in which R' is H or $C_1$-$C_8$ alkyl; $X_8$ is a linkage selected from the group consisting of

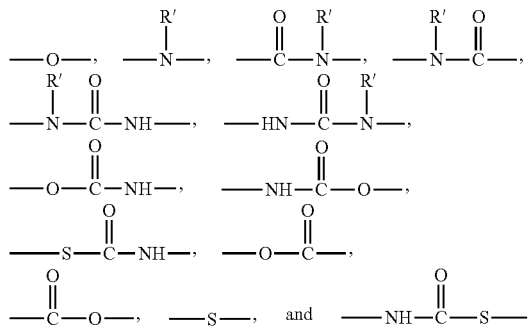

in which R' is H or $C_1$-$C_8$ alkyl; $G_5$ is a linear or branched $C_1$-$C_{10}$ alkylene divalent radical, a divalent radical of $-(\text{alk'-O})_q\text{alk-}$ as defined above, or a divalent radical of $-R'_1-X_5\text{-E-}X_6-R'_2-$ as defined above; $G_6$ is a $C_2$-$C_6$ alkylene divalent radical; LC is a divalent radical of a linear polymer chain of one or more hydrophilic vinylic monomers; and AX is a thiol group or a radical of formula $-X_8$-$G_7$-$X_9$-Q, in which: $X_8$ is an linkage as defined above; $G_7$ is a direct bond or a linear or branched alkylene divalent radical; $X_9$ is a direct bond or a linkage selected from the group consisting of

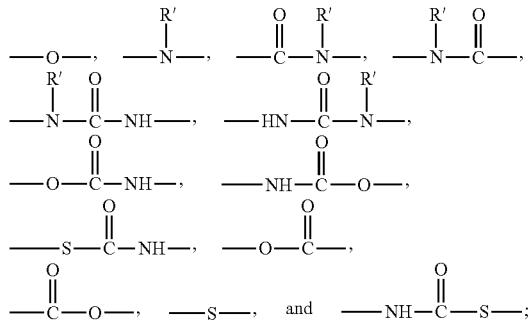

Q is an acryloyl group, a methacryloyl group, a vinyl group, an allyl group, or a norbornenyl group; and
actinically irradiating the lens forming material in the cavity to form a contact lens.

6. The contact lens of claim 1, wherein LC is a divalent radical of a linear polymer chain of one or more hydrophilic vinylic monomers selected from the group consisting of N,N-dimethylacrylamide, N,N-dimethylmethacrylamide, 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethyl methacrylate, 2-hydroxyethyl acrylate, hydroxypropyl acrylate, hydroxypropyl methacrylate, trimethylammonium 2-hydroxy propylmethacrylate hydrochloride, aminopropyl methacrylate hydrochloride, dimethylaminoethyl methacrylate, glycerol methacrylate, N-vinyl-2-pyrrolidone, allyl alcohol, vinylpyridine, acrylic acid, a $C_1$-$C_4$-alkoxy polyethylene glycol(meth)acrylate having a weight average molecular weight of up to 1500, methacrylic acid, N-vinyl formamide, N-vinyl acetamide, N-vinyl isopropylamide, N-vinyl-N-methyl acetamide, allyl alcohol, N-vinyl caprolactam, and mixtures thereof.

7. The contact lens of claim 6, wherein LC is a divalent radical of a linear polymer chain composed of monomeric units of N,N-dimethylacrylamide or N,N-dimethylacrylamide and one or more hydrophilic vinylic monomer other than N,N-dimethylacrylamide.

8. The contact lens of claim 6, wherein LC is a divalent radical of a linear polymer chain composed of monomeric units of N-Vinylpyrrolidone or N-Vinylpyrrolidone and one or more hydrophilic vinylic monomer other than N-Vinylpyrrolidone.

9. The contact lens of claim 6, wherein LC is a divalent radical of a linear polymer chain composed of monomeric units of 3-acryloylamino-1-propanol, N-hydroxyethyl acrylamide, N-[tris(hydroxymethyl)methyl]-acrylamide, 2-hydroxyethylmethacrylate (HEMA), 2-hydroxyethyl acrylate (HEA), hydroxypropyl acrylate, hydroxypropyl methacrylate (HPMA), glycerol methacrylate (GMA), allyl alcohol, a $C_1$-$C_4$-alkoxy polyethylene glycol(meth)acrylate having a weight average molecular weight of up to 1500, or a combination thereof.

10. The contact lens of claim 6, wherein the prepolymer is represented by formula (1) in which $r_2$ is zero, and $G_2$ is a linear or branched $C_1$-$C_{10}$ alkyl radical or a monovalent radical of $-(\text{alk'-O})_q\text{alk-}$ in which q and alk" are defined as above and alk" is $C_1$-$C_6$ alkyl.

11. The contact lens of claim 6, wherein the prepolymer is represented by formula (1) in which $r_2$ is an integer of 1.

12. The contact lens of claim 2, wherein LC is a divalent radical of a linear polymer chain of one or more hydrophilic vinylic monomers selected from the group consisting of N,N-dimethylacrylamide, N,N-dimethylmethacrylamide, 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethyl methacrylate, 2-hydroxyethyl acrylate, hydroxypropyl acrylate, hydroxypropyl methacrylate, trimethylammonium 2-hydroxy propylmethacrylate hydrochloride, aminopropyl methacrylate hydrochloride, dimethylaminoethyl methacrylate, glycerol methacrylate, N-vinyl-2-pyrrolidone, allyl alcohol, vinylpyridine, acrylic acid, a $C_1$-$C_4$-alkoxy polyethylene glycol(meth)acrylate having a weight average molecular weight of up to 1500, methacrylic acid, N-vinyl formamide, N-vinyl acetamide, N-vinyl isopropylamide, N-vinyl-N-methyl acetamide, allyl alcohol, N-vinyl caprolactam, and mixtures thereof.

13. The contact lens of claim 12, wherein LC is a divalent radical of a linear polymer chain composed of monomeric units of N,N-dimethylacrylamide or N,N-dimethylacrylamide and one or more hydrophilic vinylic monomer other than N,N-dimethylacrylamide.

14. The contact lens of claim 12, wherein LC is a divalent radical of a linear polymer chain composed of monomeric units of N-Vinylpyrrolidone or N-Vinylpyrrolidone and one or more hydrophilic vinylic monomer other than N-Vinylpyrrolidone.

15. The contact lens of claim 12, wherein LC is a divalent radical of a linear polymer chain composed of monomeric units of 3-acryloylamino-1-propanol, N-hydroxyethyl acrylamide, N-[tris(hydroxymethyl)methyl]-acrylamide, 2-hydroxyethylmethacrylate (HEMA), 2-hydroxyethyl acrylate (HEA), hydroxypropyl acrylate, hydroxypropyl methacrylate (HPMA), glycerol methacrylate (GMA), allyl alcohol, a $C_1$-$C_4$-alkoxy polyethylene glycol(meth)acrylate having a weight average molecular weight of up to 1500, or a combination thereof.

16. The contact lens of claim 12, wherein the prepolymer is represented by formula (1) in which $r_2$ is zero, and $G_2$ is a linear or branched $C_1$-$C_{10}$ alkyl radical or a monovalent radical of $-(alk'-O)_q alk''$ in which q and alk' are defined as above and alk'' is $C_1$-$C_6$ alkyl.

17. The contact lens of claim 12, wherein the prepolymer is represented by formula (1) in which $r_2$ is an integer of 1.

18. The contact lens of claim 3, wherein LC is a divalent radical of a linear polymer chain of one or more hydrophilic vinylic monomers selected from the group consisting of N,N-dimethylacrylamide, N,N-dimethylmethacrylamide, 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethyl methacrylate, 2-hydroxyethyl acrylate, hydroxypropyl acrylate, hydroxypropyl methacrylate, trimethylammonium 2-hydroxy propylmethacrylate hydrochloride, aminopropyl methacrylate hydrochloride, dimethylaminoethyl methacrylate, glycerol methacrylate, N-vinyl-2-pyrrolidone, allyl alcohol, vinylpyridine, acrylic acid, a $C_1$-$C_4$-alkoxy polyethylene glycol(meth)acrylate having a weight average molecular weight of up to 1500, methacrylic acid, N-vinyl formamide, N-vinyl acetamide, N-vinyl isopropylamide, N-vinyl-N-methyl acetamide, allyl alcohol, N-vinyl caprolactam, and mixtures thereof.

19. The contact lens of claim 18, wherein the prepolymer is represented by formula (1) in which $r_2$ is zero, and $G_2$ is a linear or branched $C_1$-$C_{10}$ alkyl radical or a monovalent radical of $-(alk'-O)_q alk''$ in which q and alk' are defined as above and alk'' is $C_1$-$C_6$ alkyl.

20. The contact lens of claim 18, wherein the prepolymer is represented by formula (1) in which $r_2$ is an integer of 1.

* * * * *